(12) United States Patent
Chen et al.

(10) Patent No.: US 12,170,140 B2
(45) Date of Patent: Dec. 17, 2024

(54) CUSTOMIZABLE MULTIMODALITY IMAGE HANGING PROTOCOLS

(71) Applicant: HOLOGIC, INC., Marlborough, MA (US)

(72) Inventors: Yung-Min Chen, Marlborough, MA (US); Edgar Weixiong Chen, Marlborough, MA (US); Brian Albert Garfinkel, Marlborough, MA (US); Brian Todd Matuska, Marlborough, MA (US); Nikolaos Gkanatsios, Marlborough, MA (US); Calvin J. Wong, Marlborough, MA (US); Herschel Anthony Solis, Marlborough, MA (US); Jessica Luu, Marlborough, MA (US); Stewart Schiffman, Marlborough, MA (US)

(73) Assignee: Hologic, Inc., Marlborough, MA (US)

( * ) Notice: Subject to any disclaimer, the term of this patent is extended or adjusted under 35 U.S.C. 154(b) by 543 days.

(21) Appl. No.: 17/296,287

(22) PCT Filed: Nov. 22, 2019

(86) PCT No.: PCT/US2019/062841
§ 371 (c)(1),
(2) Date: May 24, 2021

(87) PCT Pub. No.: WO2020/107019
PCT Pub. Date: May 28, 2020

(65) Prior Publication Data
US 2022/0020475 A1    Jan. 20, 2022

Related U.S. Application Data

(60) Provisional application No. 62/817,352, filed on Mar. 12, 2019, provisional application No. 62/771,127, filed on Nov. 25, 2018.

(51) Int. Cl.
*G06F 3/0482* (2013.01)
*G06F 3/04845* (2022.01)
(Continued)

(52) U.S. Cl.
CPC .......... *G16H 30/20* (2018.01); *G06F 3/0482* (2013.01); *G06F 3/04845* (2013.01);
(Continued)

(58) Field of Classification Search
None
See application file for complete search history.

(56) References Cited

U.S. PATENT DOCUMENTS 3,502,878 A    3/1970 Stewart
3,863,073 A    1/1975 Wagner
(Continued)

FOREIGN PATENT DOCUMENTS

CN    108135580    6/2018
EP    775467       5/1997
(Continued)

OTHER PUBLICATIONS

"Layer Basics—Adobe Press" Published on Apr. 6, 2017. https://www.adobepress.com/articles/article.asp?p=2756476&seqNum=4.*
(Continued)

*Primary Examiner* — Rinna Yi
(74) *Attorney, Agent, or Firm* — Merchant & Gould P.C.

(57) ABSTRACT

Systems and methods for generating and using a customized hanging protocol for the display of medical images. The methods may include receiving an indication to create a first hanging step of the hanging protocol, displaying a workspace having a plurality of viewports for displaying medical images, and displaying a plurality of building blocks corresponding to different types of medical images. The method
(Continued)

may also include receiving a selection of a first building block in the plurality of building blocks, wherein the first building block corresponds to a first type of medical image, and receiving an indication of a location in the workspace for the first building block to be placed. Based on the indication of the location in the workspace for the first building block, one or more of the plurality of viewports is filled with the first building block.

14 Claims, 32 Drawing Sheets

(51) Int. Cl.
  *G06F 3/0486* (2013.01)
  *G06F 3/04886* (2022.01)
  *G16H 30/20* (2018.01)
(52) U.S. Cl.
  CPC ........ *G06F 3/0486* (2013.01); *G06F 3/04886* (2013.01); *G06F 2203/04803* (2013.01)

(56) References Cited

U.S. PATENT DOCUMENTS

| | | | |
|---|---|---|---|
| 3,971,950 | A | 7/1976 | Evans et al. |
| 4,160,906 | A | 7/1979 | Daniels et al. |
| 4,310,766 | A | 1/1982 | Finkenzeller et al. |
| 4,496,557 | A | 1/1985 | Malen et al. |
| 4,559,641 | A | 12/1985 | Caugant et al. |
| 4,706,269 | A | 11/1987 | Reina et al. |
| 4,744,099 | A | 5/1988 | Huettenrauch et al. |
| 4,773,086 | A | 9/1988 | Fujita et al. |
| 4,773,087 | A | 9/1988 | Plewes |
| 4,819,258 | A | 4/1989 | Kleinman et al. |
| 4,821,727 | A | 4/1989 | Levene et al. |
| 4,969,174 | A | 11/1990 | Scheid et al. |
| 4,989,227 | A | 1/1991 | Tirelli et al. |
| 5,018,176 | A | 5/1991 | Romeas et al. |
| RE33,634 | E | 7/1991 | Yanaki |
| 5,029,193 | A | 7/1991 | Saffer |
| 5,051,904 | A | 9/1991 | Griffith |
| 5,078,142 | A | 1/1992 | Siczek et al. |
| 5,163,075 | A | 11/1992 | Lubinsky et al. |
| 5,164,976 | A | 11/1992 | Scheid et al. |
| 5,199,056 | A | 3/1993 | Darrah |
| 5,240,011 | A | 8/1993 | Assa |
| 5,289,520 | A | 2/1994 | Pellegrino et al. |
| 5,359,637 | A | 10/1994 | Webber |
| 5,365,562 | A | 11/1994 | Toker |
| 5,404,152 | A | 4/1995 | Nagai |
| 5,415,169 | A | 5/1995 | Siczek et al. |
| 5,426,685 | A | 6/1995 | Pellegrino et al. |
| 5,452,367 | A | 9/1995 | Bick et al. |
| 5,506,877 | A | 4/1996 | Niklason et al. |
| 5,526,394 | A | 6/1996 | Siczek et al. |
| 5,539,797 | A | 7/1996 | Heidsieck et al. |
| 5,553,111 | A | 9/1996 | Moore et al. |
| 5,592,562 | A | 1/1997 | Rooks |
| 5,594,769 | A | 1/1997 | Pellegrino et al. |
| 5,596,200 | A | 1/1997 | Sharma et al. |
| 5,598,454 | A | 1/1997 | Franetzki et al. |
| 5,609,152 | A | 3/1997 | Pellegrino et al. |
| 5,627,869 | A | 5/1997 | Andrew et al. |
| 5,657,362 | A | 8/1997 | Giger et al. |
| 5,668,889 | A | 9/1997 | Hara |
| 5,719,952 | A | 2/1998 | Rooks |
| 5,735,264 | A | 4/1998 | Siczek et al. |
| 5,769,086 | A | 6/1998 | Ritchart et al. |
| 5,803,912 | A | 9/1998 | Siczek et al. |
| 5,818,898 | A | 10/1998 | Tsukamoto et al. |
| 5,828,722 | A | 10/1998 | Ploetz et al. |
| 5,872,828 | A | 2/1999 | Niklason et al. |
| 5,878,104 | A | 3/1999 | Ploetz |
| 5,896,437 | A | 4/1999 | Ploetz |
| 5,986,662 | A | 11/1999 | Argiro et al. |
| 6,005,907 | A | 12/1999 | Ploetz |
| 6,022,325 | A | 2/2000 | Siczek et al. |
| 6,075,879 | A | 6/2000 | Roehrig et al. |
| 6,091,841 | A | 7/2000 | Rogers et al. |
| 6,137,527 | A | 10/2000 | Abdel-Malek et al. |
| 6,141,398 | A | 10/2000 | He et al. |
| 6,149,301 | A | 11/2000 | Kautzer et al. |
| 6,175,117 | B1 | 1/2001 | Komardin et al. |
| 6,196,715 | B1 | 3/2001 | Nambu et al. |
| 6,216,540 | B1 | 4/2001 | Nelson et al. |
| 6,219,059 | B1 | 4/2001 | Argiro |
| 6,233,473 | B1 | 5/2001 | Shepherd et al. |
| 6,243,441 | B1 | 6/2001 | Zur |
| 6,256,370 | B1 | 7/2001 | Yavuz |
| 6,272,207 | B1 | 8/2001 | Tang |
| 6,289,235 | B1 | 9/2001 | Webber et al. |
| 6,292,530 | B1 | 9/2001 | Yavus et al. |
| 6,327,336 | B1 | 12/2001 | Gingold et al. |
| 6,341,156 | B1 | 1/2002 | Baetz et al. |
| 6,375,352 | B1 | 4/2002 | Hewes et al. |
| 6,411,836 | B1 | 6/2002 | Patel et al. |
| 6,415,015 | B2 | 7/2002 | Nicolas et al. |
| 6,442,288 | B1 | 8/2002 | Haerer et al. |
| 6,459,925 | B1 | 10/2002 | Nields et al. |
| 6,501,819 | B2 | 12/2002 | Unger et al. |
| 6,515,685 | B1 | 2/2003 | Halverson |
| 6,525,713 | B1 | 2/2003 | Soeta et al. |
| 6,556,655 | B1 | 4/2003 | Chichereau et al. |
| 6,597,762 | B1 | 7/2003 | Ferrant et al. |
| 6,611,575 | B1 | 8/2003 | Alyassin et al. |
| 6,620,111 | B2 | 9/2003 | Stephens et al. |
| 6,626,849 | B2 | 9/2003 | Huitema et al. |
| 6,633,674 | B1 | 10/2003 | Barnes et al. |
| 6,638,235 | B2 | 10/2003 | Miller et al. |
| 6,647,092 | B2 | 11/2003 | Eberhard et al. |
| 6,744,848 | B2 | 6/2004 | Stanton et al. |
| 6,748,044 | B2 | 6/2004 | Sabol et al. |
| 6,751,285 | B2 | 6/2004 | Eberhard et al. |
| 6,751,780 | B1* | 6/2004 | Neff .................. H04N 1/3873 382/229 |
| 6,758,824 | B1 | 7/2004 | Miller et al. |
| 6,813,334 | B2 | 11/2004 | Koppe et al. |
| 6,882,700 | B2 | 4/2005 | Wang et al. |
| 6,885,724 | B2 | 4/2005 | Li et al. |
| 6,912,319 | B1 | 6/2005 | Barnes et al. |
| 6,940,943 | B2 | 9/2005 | Claus et al. |
| 6,978,040 | B2 | 12/2005 | Berestov |
| 6,999,554 | B2 | 2/2006 | Mertelmeier |
| 7,025,725 | B2 | 4/2006 | Dione et al. |
| 7,110,490 | B2 | 9/2006 | Eberhard |
| 7,110,502 | B2 | 9/2006 | Tsuji |
| 7,123,684 | B2 | 10/2006 | Jing et al. |
| 7,127,091 | B2 | 10/2006 | Op De Beek et al. |
| 7,142,633 | B2 | 11/2006 | Eberhard et al. |
| 7,245,694 | B2 | 7/2007 | Jing et al. |
| 7,315,607 | B2 | 1/2008 | Ramsauer |
| 7,319,735 | B2 | 1/2008 | Defreitas et al. |
| 7,323,692 | B2 | 1/2008 | Rowlands et al. |
| 7,430,272 | B2 | 9/2008 | Jing et al. |
| 7,443,949 | B2 | 10/2008 | Defreitas et al. |
| 7,577,282 | B2 | 8/2009 | Gkanatsios et al. |
| 7,606,801 | B2 | 10/2009 | Faitelson et al. |
| 7,630,533 | B2 | 12/2009 | Ruth et al. |
| 7,702,142 | B2 | 4/2010 | Ren et al. |
| 7,760,924 | B2 | 7/2010 | Ruth et al. |
| 7,840,905 | B1* | 11/2010 | Weber .................. G06F 40/166 715/765 |
| 8,239,784 | B2 | 8/2012 | Hotelling |
| 8,571,289 | B2 | 10/2013 | Ruth et al. |
| 8,712,127 | B2 | 4/2014 | Ren et al. |
| 8,799,013 | B2 | 8/2014 | Gustafson |
| 8,842,806 | B2 | 9/2014 | Packard |
| 9,084,579 | B2 | 7/2015 | Ren |
| 9,795,357 | B2 | 10/2017 | Carelsen |
| 9,811,758 | B2 | 11/2017 | Ren |
| 9,962,138 | B2 | 5/2018 | Schweizer |
| 10,076,295 | B2 | 9/2018 | Gemmel |

(56) References Cited

U.S. PATENT DOCUMENTS

| | | | |
|---|---|---|---|
| 10,111,631 B2 | 10/2018 | Gkanatsios et al. |
| 10,206,644 B2 | 2/2019 | Kim |
| 10,248,882 B2 | 4/2019 | Ren |
| 10,679,095 B2 | 6/2020 | Ren |
| 10,922,897 B2 | 2/2021 | Maeda |
| 11,650,672 B2 | 5/2023 | Mellett |
| 11,857,358 B2 | 1/2024 | Liu |
| 2001/0038681 A1 | 11/2001 | Stanton et al. |
| 2001/0038861 A1 | 11/2001 | Hsu et al. |
| 2002/0012450 A1 | 1/2002 | Tsujii |
| 2002/0050986 A1 | 5/2002 | Inoue et al. |
| 2002/0075997 A1 | 6/2002 | Unger et al. |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0149364 A1 | 8/2003 | Kapur |
| 2003/0194050 A1 | 10/2003 | Eberhard et al. |
| 2003/0194051 A1 | 10/2003 | Wang et al. |
| 2003/0194115 A1 | 10/2003 | Kaufhold et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0001094 A1* | 1/2004 | Unnewehr ............ G06F 3/0486 |
| | | 715/769 |
| 2004/0008809 A1 | 1/2004 | Webber |
| 2004/0066882 A1 | 4/2004 | Eberhard et al. |
| 2004/0066884 A1 | 4/2004 | Hermann Claus et al. |
| 2004/0066904 A1 | 4/2004 | Eberhard et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | Defreitas et al. |
| 2005/0078797 A1 | 4/2005 | Danielsson et al. |
| 2005/0089205 A1 | 4/2005 | Kapur |
| 2005/0105679 A1 | 5/2005 | Wu et al. |
| 2005/0113681 A1 | 5/2005 | DeFreitas |
| 2005/0113715 A1 | 5/2005 | Schwindt et al. |
| 2005/0129172 A1 | 6/2005 | Mertelmeier |
| 2005/0135555 A1 | 6/2005 | Claus et al. |
| 2005/0135664 A1 | 6/2005 | Kaufhold et al. |
| 2005/0140656 A1 | 6/2005 | McLoone |
| 2005/0226375 A1 | 10/2005 | Eberhard et al. |
| 2006/0026535 A1 | 2/2006 | Hotelling |
| 2006/0030784 A1 | 2/2006 | Miller et al. |
| 2006/0074288 A1 | 4/2006 | Kelly et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0291618 A1 | 12/2006 | Eberhard et al. |
| 2007/0030949 A1 | 2/2007 | Jing et al. |
| 2007/0036265 A1 | 2/2007 | Jing et al. |
| 2007/0076844 A1 | 4/2007 | Defreitas et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0021877 A1 | 1/2008 | Saito |
| 2008/0045833 A1 | 2/2008 | Defreitas et al. |
| 2008/0109740 A1 | 5/2008 | Prinsen et al. |
| 2008/0130979 A1 | 6/2008 | Ren et al. |
| 2008/0187095 A1 | 8/2008 | Boone |
| 2008/0262874 A1 | 10/2008 | Toshimutsu |
| 2008/0267467 A1 | 10/2008 | Sokulin et al. |
| 2009/0003519 A1 | 1/2009 | Defreitas et al. |
| 2009/0010384 A1 | 1/2009 | Jing et al. |
| 2009/0033522 A1 | 2/2009 | Skillman |
| 2009/0080594 A1 | 3/2009 | Brooks et al. |
| 2009/0080602 A1 | 3/2009 | Brooks et al. |
| 2009/0135997 A1 | 5/2009 | Defreitas et al. |
| 2009/0174663 A1 | 7/2009 | Rudd |
| 2009/0213034 A1 | 8/2009 | Wu et al. |
| 2009/0268865 A1 | 10/2009 | Ren et al. |
| 2009/0296882 A1 | 12/2009 | Gkanatsios et al. |
| 2009/0304147 A1 | 12/2009 | Jing et al. |
| 2010/0054400 A1 | 3/2010 | Ren et al. |
| 2010/0083154 A1 | 4/2010 | Takeshita |
| 2010/0086188 A1 | 4/2010 | Ruth et al. |
| 2010/0135558 A1 | 6/2010 | Ruth et al. |
| 2010/0194682 A1 | 8/2010 | Orr |
| 2010/0195882 A1 | 8/2010 | Ren et al. |
| 2010/0226475 A1 | 9/2010 | Smith et al. |
| 2010/0325088 A1 | 12/2010 | Hsieh et al. |
| 2011/0137132 A1 | 6/2011 | Gustafson |
| 2011/0270358 A1 | 11/2011 | Davis |
| 2011/0282686 A1 | 11/2011 | Venon |
| 2011/0314405 A1 | 12/2011 | Turner |
| 2012/0131498 A1 | 5/2012 | Gross et al. |
| 2012/0133600 A1 | 5/2012 | Marshall et al. |
| 2012/0154431 A1 | 6/2012 | Fram |
| 2012/0275656 A1 | 11/2012 | Boese et al. |
| 2013/0239063 A1* | 9/2013 | Ubillos ................ G06F 3/0485 |
| | | 715/838 |
| 2013/0259193 A1 | 10/2013 | Packard |
| 2014/0013280 A1 | 1/2014 | Yoshioka et al. |
| 2014/0033126 A1 | 1/2014 | Kreeger |
| 2014/0123183 A1 | 5/2014 | Fujimoto |
| 2014/0140604 A1 | 5/2014 | Carton et al. |
| 2014/0143710 A1* | 5/2014 | Zhao ...................... G16H 30/40 |
| | | 715/835 |
| 2014/0282216 A1* | 9/2014 | Baker ................... G16H 40/63 |
| | | 715/781 |
| 2014/0314205 A1 | 10/2014 | Carelsen |
| 2015/0094581 A1 | 4/2015 | Butler |
| 2015/0260816 A1 | 9/2015 | Liang |
| 2015/0309712 A1 | 10/2015 | Marshall et al. |
| 2015/0317434 A1* | 11/2015 | Kondo .................. A61B 6/463 |
| | | 705/3 |
| 2015/0374325 A1 | 12/2015 | Shimizu |
| 2016/0162163 A1 | 6/2016 | Park et al. |
| 2016/0166222 A1 | 6/2016 | Kim |
| 2016/0235386 A1 | 8/2016 | Schweizer |
| 2016/0296185 A1 | 10/2016 | Gemmel |
| 2016/0364122 A1* | 12/2016 | Shimomura .......... G06F 3/0481 |
| 2016/0367120 A1 | 12/2016 | Dupont et al. |
| 2017/0038914 A1* | 2/2017 | Kawagishi ............ G16H 30/40 |
| 2017/0065238 A1 | 3/2017 | Smith et al. |
| 2018/0137385 A1 | 5/2018 | Ren |
| 2018/0211421 A1 | 7/2018 | Wicklein |
| 2019/0196662 A1 | 6/2019 | Mitchell |
| 2019/0221046 A1 | 7/2019 | Maeda |
| 2019/0325255 A1 | 10/2019 | Ren |
| 2020/0363877 A1 | 11/2020 | Mellett |
| 2020/0373013 A1 | 11/2020 | Cao |
| 2022/0015731 A1 | 1/2022 | Liu |
| 2022/0172824 A1 | 6/2022 | Solis |
| 2023/0107616 A1 | 4/2023 | Saba |

FOREIGN PATENT DOCUMENTS

| | | |
|---|---|---|
| EP | 982001 | 3/2000 |
| EP | 1004957 | 5/2000 |
| EP | 1428473 | 6/2004 |
| EP | 2783632 | 10/2014 |
| EP | 2913769 | 9/2015 |
| EP | 2952376 | 12/2015 |
| JP | 2000-322198 | 11/2000 |
| JP | 2004-038947 | 2/2004 |
| JP | 2004-357789 | 12/2004 |
| JP | 2007-029260 A | 2/2007 |
| JP | 2007-282656 | 11/2007 |
| JP | 2007-330374 | 12/2007 |
| JP | 2008-503253 | 2/2008 |
| JP | 2008-073436 | 4/2008 |
| JP | 2008-199293 | 8/2008 |
| JP | 2010-086149 | 4/2010 |
| JP | 2014-068874 | 4/2014 |
| JP | 2014-104099 | 6/2014 |
| JP | 2017-000664 | 1/2017 |
| WO | 1990/05485 | 5/1990 |
| WO | 1998/16903 | 4/1998 |

(56) References Cited

FOREIGN PATENT DOCUMENTS

| WO | 00/51484 | 9/2000 |
|---|---|---|
| WO | 03/020114 | 3/2003 |
| WO | 2005/051197 | 6/2005 |
| WO | 2005/110230 | 11/2005 |
| WO | 2005/112767 | 12/2005 |
| WO | 2006/055830 | 5/2006 |
| WO | 2006/058160 | 6/2006 |
| WO | 2011/044295 | 4/2011 |
| WO | 2011/066486 | 6/2011 |
| WO | 2012/071429 | 5/2012 |
| WO | 2014/183183 | 11/2014 |
| WO | 2018/183548 | 10/2018 |
| WO | 2018/183549 | 10/2018 |
| WO | 2018/183550 | 10/2018 |
| WO | 2019/032558 | 2/2019 |

OTHER PUBLICATIONS

International Search Report and Written Opinion of the International Searching Authority for International Patent Application No. PCT/US2019/062841 mailed Apr. 22, 2020, 19 pages.

PCT International Preliminary Report on Patentability in International Application PCT/US2019/062841, mailed Jun. 3, 2021, 13 pages.

Cole, Elodia, et al., "The Effects of Gray Scale Image Processing on Digital Mammography Interpretation Performance", Academic Radiology, vol. 12, No. 5, pp. 585-595, May 2005.

Digital Clinical Reports, Tomosynthesis, GE Brochure 98/5493, Nov. 1998.

Dobbins JT et al. "Digital x-ray tom osynthesis: current state of the art and clinical potential" Physics in Medicine and Biology vol. 48, No. 19, pp. 65-81 (2003).

Essentials for life: Senographe Essential Full-Field Digital Mammography System, GE Health-care Brochure, MM-0132-05.06-ENUS, 2006.

Filtered Back Projection, (NYGREN) published May 8, 2007;URL: http://web.archive.org/web/1999101013 I 715/http://www.owlnet.rice.edu/-elec539/Projects97/cult/node2.html.

Grant, DG, "Tomosynthesis, a three dimensional imagine technique", IEEE Trans. Biomed Engineering, vol. BME-19, #1, Jan. 1972, pp. 20-28.

Heang-Ping Chan et al., "ROC study of the effect of stereoscopic imaging on assessment of breast lesions", Medical Physics, vol. 32, No. 4, Apr. 2005.

Kita et al., "Correspondence between different view breast X-rays using simulation of breast deformation", Proceedings 1998 IEE Computer Society Conference on Computer Vision and Pattern Recognition, Santa Barbara, CA, Jun. 23-25, 1998, pp. 700-707.

Lorad Selenia Document B-BI-SEO US/Intl (May 2006) copyright Hologic 2006.

Mammographic Accreditation Phantom, http://www.cirsinc.com/pdfs/015cp.pdf.

Pediconi, Federica et al., "Color-coded automated signal intensity curve for detection and characterization of breast lesions: Preliminary evaluation of a new software for MR-based breast imaging", International Congress Series 1281 (2005) 1081-1086.

Senographe 700 & 800T (GE); 2-page download on Jun. 22, 2006 from www.gehealthcare.com/inen/rad/whe/products/mswh800t.html.; Figures 1-7 on 4 sheets relateral shift compression paddle.

Smith, A., "Fundamentals of Breast Tomosynthesis", White Paper, Hologic Inc., WP-00007, Jun. 2008.

\* cited by examiner

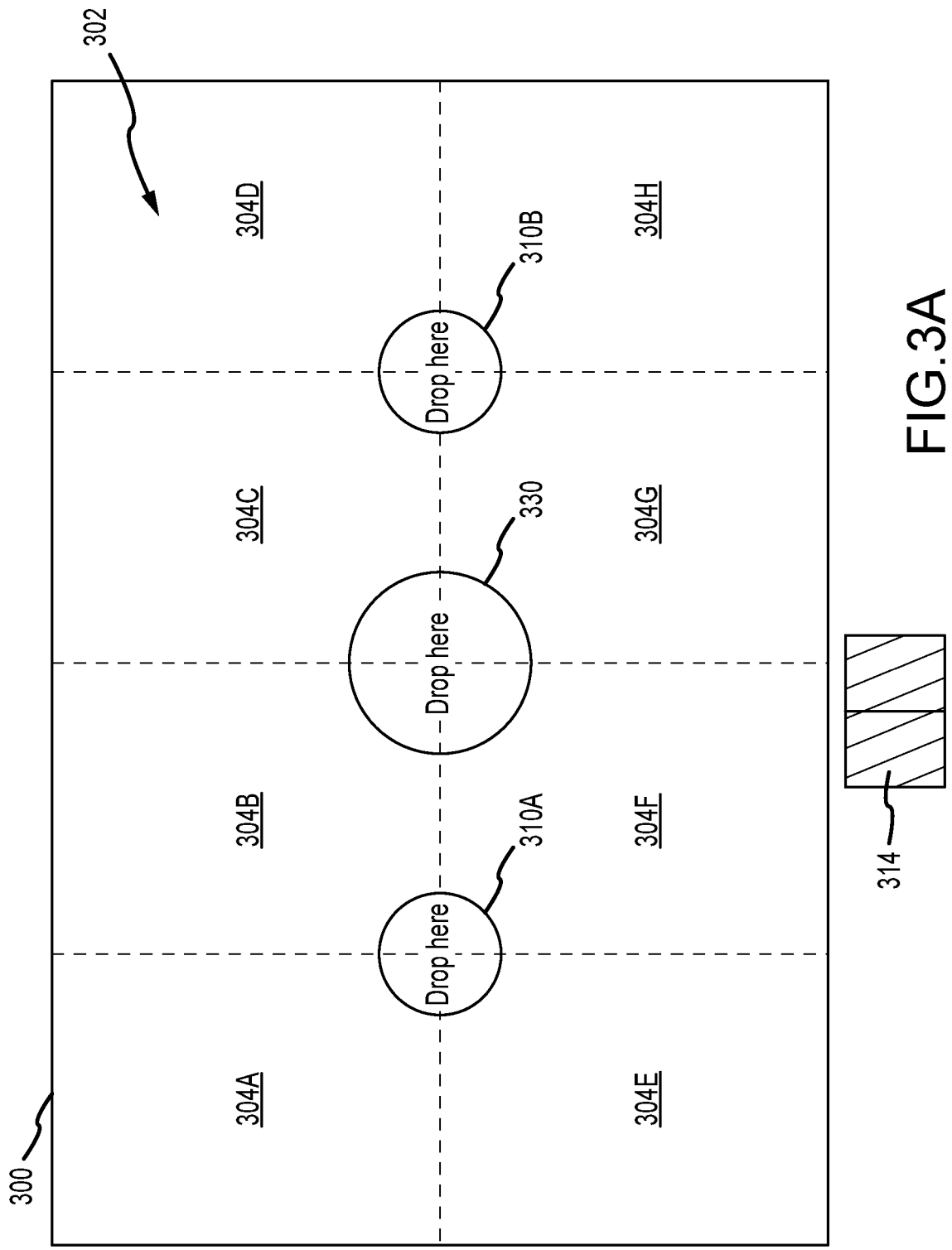

| PRIVATE TAG 1 for Labels | | | | | Private Header Tag in Each Digit | | | | |
|---|---|---|---|---|---|---|---|---|---|
| Labels (First level) | Labels (Second level) | Labels (Third level) | Qualifiers | Qualifier Version | A | B | C | D | E |
| T$_1$-weighted Sequence | Non FAT SAT | | | | 1 | 1 | | | |
| | FAT SAT | | | | | 2 | | | |
| | | Low Spatial | | | | | 1 | | |
| | | High Spatial | | | | | 2 | | |
| | | | | | | | | | |
| T$_2$-weighted Sequence | Non FAT SAT | | | | 2 | 1 | | | |
| | FAT SAT | | | | | 2 | | | |
| | | Low Spatial | | | | | 1 | | |
| | | High Spatial | | | | | 2 | | |
| | | | | | | | | | |
| Dynamic Sequence | Non FAT SAT | | | | 3 | 1 | | | |
| | FAT SAT | | | | | 2 | | | |
| | | Low Temporal | | | | | 1 | | |
| | | High Temporal | | | | | 2 | | |
| | | Abbreviated | | | | | 3 | | |
| | | | MOCO | | | | | 1 | |
| | | | | Version | | | | | 1 |
| | | | | | | | | | |
| Diffusion Weighted Sequence | Non FAT SAT | | | | 4 | 1 | | | |
| | FAT SAT | | | | | 2 | | | |
| | | Diffusion | | | | | 1 | | |
| | | Tensor | | | | | 2 | | |
| | | | MOCO | | | | | 1 | |
| | | | | Version | | | | | 1 |
| | | | | | | | | | |
| Susceptibility Weighted Sequence | Non FAT SAT | | | | 5 | 1 | | | |
| | FAT SAT | | | | | 2 | | | |
| | | Magnitude | | | | | 1 | | |
| | | Phase | | | | | 2 | | |
| | | | | | | | | | |
| Miscellaneous | | | | | 6 | | | | |

Sample Tag #1: | 3 | 2 | 1 | 1 | 2 |

Sample Tag #2:

| 2 | 2 | 2 |
|---|---|---|

PRIVATE TAG 2 for mapping (904)

| Mapping Types | Mapping Labels | Mapping Version | Private Header Tag in Each Digit | | |
|---|---|---|---|---|---|
| | | | A | B | C |
| Diffusion | ADC | | 1 | 1 | |
| | Direction | | | 2 | |
| | Vector | | | 3 | |
| DCE | DCE | | 2 | 1 | |
| | KTRANS | | | 2 | |
| | KEP | | | 3 | |
| | IAUC90 | | | 4 | |
| | | Pixel Value Based | | | 1 |
| | | Concentration | | | 2 |

FIG.9B

CUSTOMIZABLE MULTIMODALITY IMAGE HANGING PROTOCOLS

CROSS-REFERENCE TO RELATED APPLICATIONS

This application is a National Stage Application of PCT/US2019/062841, filed on Nov. 22, 2019, which claims priority to and the benefit of U.S. Provisional Application No. 62/817,352, titled "Multimodality Hanging Protocols," filed on Mar. 12, 2019, and U.S. Provisional Application No. 62/771,127, titled "Multimodality Hanging Protocols," filed on Nov. 25, 2018. Those applications are incorporated herein by reference in their entireties. To the extent appropriate, a claim of priority is made to each of the above disclosed applications.

INTRODUCTION

Medical imaging procedures are often used to screen, detect, or diagnose abnormalities within the human body. For instance, mammography or tomosynthesis imaging techniques are often used for screening for breast cancer. Once the images are acquired through a mammography or tomography imaging device, however, the images must be analyzed to determine if there are any abnormalities within the breast. That analysis is commonly performed by a radiologist. Each radiologist may have a particular procedure for which he or she requires or prefers to perform the analysis of the images. In the past, with film-based images, the radiologist would physically "hang" each of the physical films in a light box to perform the analysis. The manner in which the physical films were hung was referred to as a "hanging protocol."

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for creation of customized hanging protocols for displaying medical images of a patient. In an aspect, the technology relates to a computer-implemented method for generating a customized hanging protocol for the display of medical images. The method includes receiving an indication to create a first hanging step of the hanging protocol; displaying a workspace having a plurality of viewports for displaying medical images; displaying a plurality of building blocks corresponding to different types of medical images; receiving a selection of a first building block in the plurality of building blocks, wherein the first building block corresponds to a first type of medical image; receiving an indication of a location in the workspace for the first building block to be placed; and based on the indication of the location in the workspace for the first building block, filling one or more of the plurality of viewports with the first building block. The method also includes receiving a selection of a second building block in the plurality of building blocks, wherein the second building block corresponds to a second type of medical image; receiving an indication of a location in the workspace for the second building block to be placed; based on the indication of the location in the workspace for the second building block; and storing the first hanging step of the hanging protocol for importation of medical images of a patient according to the filled viewports in the workspace.

In an example, the first building block corresponds to a first imaging modality and the second building block corresponds to a second imaging modality. In another example, the workspace includes a plurality of hotspots, each of the hotspots configured to expand a building block across at least two viewports. In yet another example, the plurality of hotspots include at least one of a column hotspot, a row hotspot, a quadruple hotspot, or an octuple hotspot. In still another example, the indication of a location in the workspace for the first building block is received via a drag and drop interaction. In still yet another example, the method also includes displaying a drop zone outline based on the type of building block.

In another example, the first building block is a composite building block. In yet another example, the plurality of building blocks are displayed in an editor bar with a plurality of building block category options. In still another example, the method further includes, based on the type of the first building block, updating the layout of the workspace upon selection the first building block. In still yet another example, the method further includes, receiving an indication to create a second hanging step of the hanging protocol; displaying a second workspace having a plurality of viewports for displaying medical images; displaying a plurality of building blocks corresponding to different types of medical images; receiving a selection of a third building block in the plurality of building blocks; receiving an indication of a location in the second workspace for the third building block to be placed; based on the indication of the location in the second workspace for the third building block, filling one or more of the plurality of viewports with the first building block; and storing the second hanging step of the hanging protocol for importation of medical images of a patient according the filled viewports in the workspace.

In another example, the method further includes displaying, within a viewport filled with the first building block, a layer option for editing a stack of images associated with the first building block; receiving a selection of the layer option; upon receiving the selection of the layer option, displaying an layer ordering menu that includes a plurality of stacked layers corresponding to medical images; receiving an indication to reorder the stacked layers; and storing the reordering of stacked layers. In yet another example, the method further includes receiving a selection of a patient for which medical images are to be imported; accessing the stored hanging protocol; importing the medical images for the patient; and displaying the imported medical images according to the stored hanging protocol.

In another aspect, the technology relates to a computer-implemented method for displaying medical images according to a stored hanging protocol. The method includes receiving a selection of a patient for which medical images are to be imported; receiving a selection stored hanging protocol; importing the medical images for the patient; displaying the imported medical images according to the stored hanging protocol; displaying a set of tools for analyzing or modifying the displayed medical images; receiving an indication to add a selected tool of the set of tools in a shortcut section; in response to receiving the indication, adding the selected tool to the shortcut section; and based on adding the selected tool to the shortcut section, making the tool available in a secondary selection menu when a secondary selection input is received.

In an example, the secondary selection input is at least one of a right-click of an input device or a long-press of a touch screen. In another example, the shortcut section is displayed in a chrome displayed adjacent to the displayed medical images. In yet another example, the selected tool is one of magnification, continuous zoom, ellipse, ruler, reset, or close study.

In another aspect, the technology relates to a computer-implemented method for generating a customized hanging protocol for displaying medical images. The method includes displaying a workspace comprising a plurality of viewports and hotspots; displaying a plurality of building blocks corresponding to different types of medical images; receiving a selection of a first building block of the plurality of building blocks; receiving a dragging indication of the first building block across the workspace; while the first building block is dragged across the workspace, display and dynamically update a drop zone outline based on a location of the building block relative to the workspace as it is being dragged, wherein the drop zone outline highlights one or more of the plurality of viewports for which the first building block will fill if it were dropped at the location. In an example, the location is over a hotspot, and the drop zone outline highlights multiple viewports. In another example, the method further includes receiving a selection of a second building block; and based on the dimensions of the second building block, altering or removing from the display at least one of the displayed hotspots.

In another aspect, the technology relates to a system for displaying medical images. The system includes a cluster of workstations, each of the workstations within the cluster being in communication with one another, wherein a first workstation is the cluster is configured to be a super node and a second workstation in the cluster is configured to be a standby super node, the super node storing patient database. The system also includes a load balancer in communication with at least one of the workstations in the cluster of workstations and a picture archive and communication system (PACS), wherein the load balancer is configured to propagate Digital Imaging and Communications in Medicine (DICOM) objects to at least one of the workstations within the cluster of workstations via a distributed downloading protocol.

In another aspect, the technology relates to a computer-implemented method for displaying medical images. The method includes accessing MRI data; analyzing the MRI data to categorize the MRI data; generating a first label for the MRI data, the first label including a first digit representing a first level of information of the MRI data and a second digit representing a second level of information of the MRI data; receiving a request to display a specific type of MRI image; based on the generated first label, identifying the MRI data as the specific type of MRI image; and displaying the MRI data in response to the request to display the specific type of MRI image.

In an example, the first level of information relates to the basic functional type of the MRI data. In another example, the first digit of the first label represents one of: a T1-weighted sequence, a T2-weighted sequence, a diffusion weighted sequence, or a susceptibility weighted sequence. In still another example, the second level of information relates to whether fat saturation has been used in the MRI data. In yet another example, the first label includes a third digit representing a third level of information of the MRI data. In still yet another example, the third level of information relates to subtypes of the functional data type represented by the first digit of the first label.

In another example, the third digit represents one of: low spatial resolution, high spatial resolution, low temporal resolution, or high temporal resolution. In still another example, the label includes a fourth digit representing a fourth level of information of the MRI data. In yet another example, the first label includes a fourth digit representing a fourth level of information of the MRI data. In still yet another example, the fourth level of information relates to motion correction. In another example, the fourth digit represents whether motion correction was performed on the MRI data.

In another example, the method further includes generating a second label for the MRI data, the second label representing characteristics of a mapping generated for the MRI data; identifying a map for the identified MRI data based on the second label; and displaying the identified map as an overlay of the MRI data. In still another example, the second label includes a first digit that represents a mapping type and a second digit that represents additional mapping labels. In yet another example, the first digit of the second label represents once of: a dynamic contrast enhancement (DCE) mapping or a diffusion mapping. In still yet another example, the second digit of the second label represents one of: an ADC mapping, a direction mapping, or a vector mapping.

In another aspect, the technology relates to a method for displaying orientation data for medical imagery. The method includes accessing a first medical image; determining a first orientation of the first medical image; generating a first orientation indicator for the determined orientation, wherein the orientation indicator is an image of a human figurine in the determined first orientation; and concurrently displaying the first medical image and the first orientation indicator.

In an example, the method further includes accessing a second medical image; determining a second orientation of the second medical image, the second orientation being different from the first orientation; generating a second orientation indicator for the determined orientation, wherein the orientation indicator is an image of a human figurine in the determined first orientation; and concurrently displaying the second medical image and the second orientation indicator. In another example, the method further includes receiving an interaction with the displayed first orientation indicator; based on the interaction, determining a new orientation; retrieving a second medical image corresponding to the determined new orientation; displaying the retrieved second medical image. In yet another example, the interaction is a drag or swipe.

In another aspect, the technology relates to a method that includes accessing a medical image having an image type; displaying a compact image reference identifier indicating the type for the medical image; displaying, adjacent to the compact image reference identifier, an elapsed time indicator that indicates a time that elapsed since the medical image was acquired; and displaying, adjacent to the compact image reference identifier, a prior image indicator that indicates a prior image number for the accessed medical image. In an example, the elapsed time indicator is displayed as a superscript to the compact image reference identifier. In another example, the prior image indicator is displayed as a subscript to the compact image reference identifier.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

FIG. 3A depicts an example user interface for creating a multimodality hanging protocol with a composite building block.

FIG. 9A depicts an example first label and table defining the first label.

FIG. 9B depicts an example second label and table defining the second label.

DETAILED DESCRIPTION

Figure 1A:
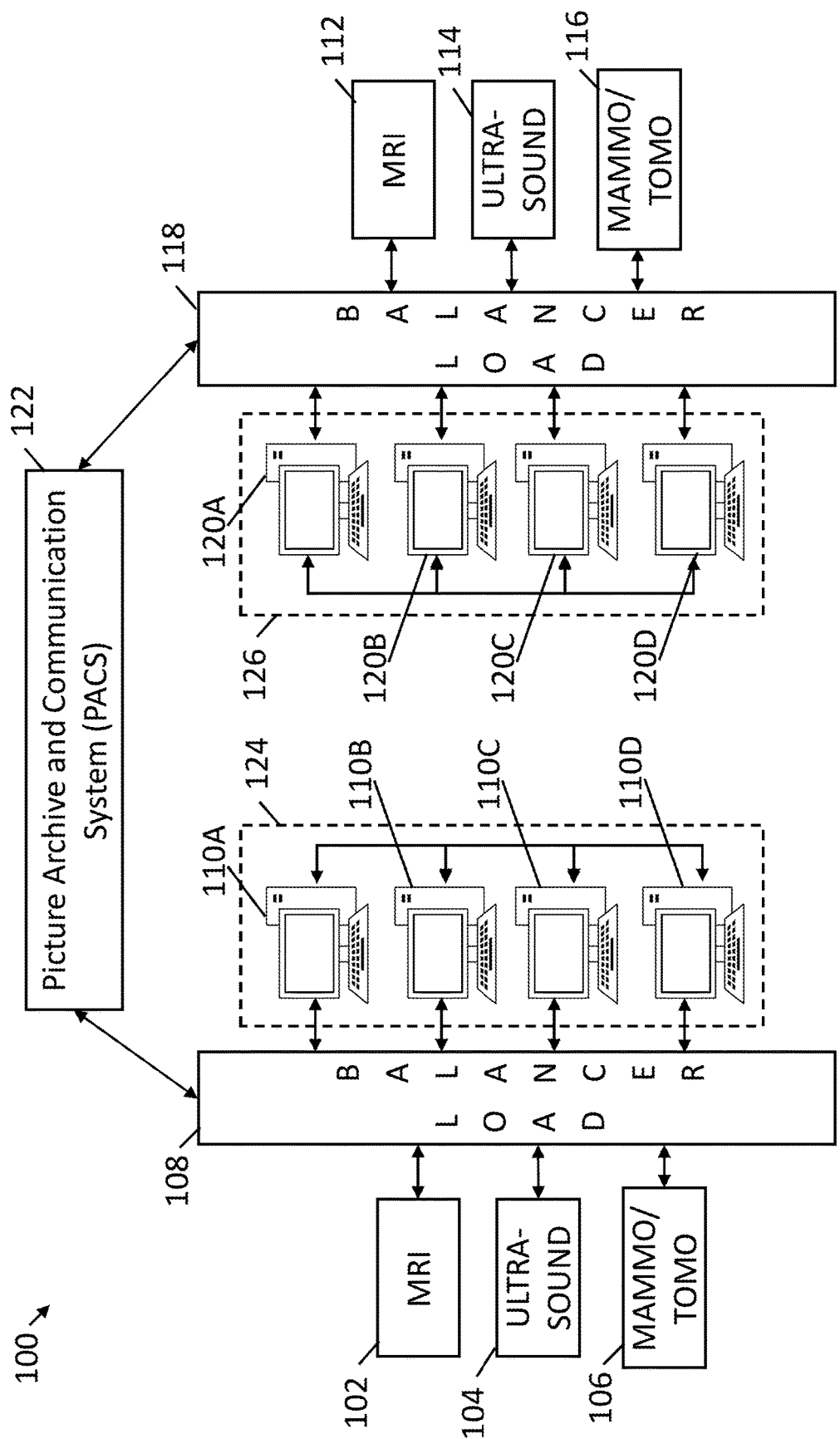
FIG. 1A depicts a system for generating and using a multimodality hanging protocol.

With the creation of digital imaging, new systems and methods need to be generated to allow for the efficient review and analysis of digital medical images. While some digital hanging protocols do exist, the creation and use of those hanging protocols is difficult, unsatisfactory, or impossible for some radiologists who work with many digital images of various types (e.g., mammography, tomosynthesis, magnetic resonance imaging (MRI), computed tomography (CT), ultrasound, nuclear medicine imaging, positron-emission tomography (PET), etc.). Existing hanging protocol tools are based on predefined steps and fixed layouts that are not customizable by the radiologist. The rigid structure of such tools lead to less efficient and effective review of medical images for some radiologists. In addition, the existing hanging protocol tools were generally limited to a single imaging modality, such as mammography. The display of multiple modalities within the same screen may provide a wealth of additional knowledge to the radiologist. As such, there is need to provide tools for generating a customizable multimodality hanging protocol that can provide a more efficient and effective display of medical images for analysis by radiologists, even where each radiologist may have different requirements for the display of such images.

The present technology provides such tools in the form of systems and methods for generating a customizable multimodality hanging protocol that can be directly edited by the radiologist. A radiologist may start by selecting a new hanging protocol to generate. The hanging protocol may include a series of hanging steps, and the radiologist may customize the number of steps as well as the display for each of the steps. The display for each step may begin as a workspace that can be filled by the radiologist for the respective views the radiologist requires or desires to complete his or her analysis. For example, the workspace may include a smart grid that guides the creation of the workspace, and the workspace may be populated by dragging and dropping building blocks thereon. Each building block may correspond to a particular view and modality. For instance, one building block may correspond to a cranio-caudal (CC) view of a left breast and another building block may correspond to an axial view of a magnetic resonance (MR) image. The smart grid may also adjust automatically based on the type of building block that is selected. The location of where the building block is dropped on the smart grid may also alter the size of the image when ultimately displayed. Once the workspace for the first hanging step is populated, a workspace for a second hanging step may be populated. The process continues until the radiologist has developed the desired number of hanging steps. The customized hanging protocol may then be saved or stored. When the radiologist then selects a patient for which to view images, the saved customized hanging protocol is used to display the images for the patient. The saved customized hanging protocol may also be shared with other radiologists and may be automatically modified based on saved preferences for the other radiologists. Tools for enhancing displayed images, such as measurement and magnification tools, may also be customized.

FIG. 1A depicts a system 100 for generating and using a multimodality hanging protocol. The system 100 includes a plurality of medical imaging devices, such as a first magnetic resonance imaging (MRI) machine 102, a first ultrasound imaging machine 104, and a first mammogram/tomosynthesis imaging machine 106. While not depicted, other types of imaging devices, such as computed tomography (CT) or positron-emission tomography (PET), may also be included. The medical imaging devices are configured to generate medical images of at least some portions of a patient. The output of the medical imaging devices is generally a plurality of images. The images from the various medical imaging devices are communicated to a first load balancer 108. The first load balancer 108 may then communicate the medical images from the medical imaging devices to a picture archive and communication system (PACS) and/or one or more workstations 110A-D to allow for viewing and analysis of the images. In some examples, the first load balancer 108 may be omitted and the images from the medical imaging devices may be communicated directly to the PACS 122 and/or one or more of the workstations 110A-D. In addition, in some examples, some of the medical imaging devices may not have a network connection to the first load balancer 108 or the workstations 110A-D. In such examples, the medical images from those medical imaging devices may be communicated to the PACS 122 and then accessed by the workstations 110A-D via the PACS 122.

The workstations 110A-D are organized in a first cluster 124. The cluster 124 of workstations 110A-D is typically indicative of each of the workstations 110A-D being able to communicate with each other workstation 110A-D. Often, all the workstations 110A-D within the cluster are located within the same facility and may be able to communicate within one another on local network at a higher bandwidth than communications with devices located outside the facility. In some examples, one or more of the workstations 110A-D may be located physically remote from one another but still located within the same network. Within the cluster 124, one of the workstations 110A-D may be designated as a super node. For example, workstation 110A may be designated as a super node. The remaining workstations 110B-D are designated as regular nodes. One of the workstations 110B-D, such as workstation 110B, may also be designated as a standby super node. A patient database may be stored on the super node and may also be replicated or mirrored to the standby super node to support high availability. Thus, in the event of a super node failure, all calls to the supernode may be automatically redirected to the standby super node. Automatically redirecting the calls to the standby super node may be accomplished through a failover feature programmed into the load balancer 108.

The database services may be exposed through the use a database application programming interface (API). As one example the, RESTful API may be used. The RESTful API is based on representational state transfer (REST) technology, and generally uses HyperText Transfer Protocol (HTTP) operations and requests such as GET, PUT, POST and DELETE data. To increase scalability and performance, Digital Imaging and Communications in Medicine (DICOM) requests to and from external devices, such as PACS, are load balanced by the load balancer 108. For example, DICOM storage requests from external devices may be routed to every node in the cluster 108. The DICOM objects received may be propagated to all nodes in the cluster using a distributed downloading protocol, such as the BITTORRENT protocol. The database may then be updated by the receiving node by calling the database service API of the super node. Every node in the cluster 124 may then retrieve the patient list from the super node through service API calls and open images stored locally to achieve higher performance. The patient list mat be a subset of patients that are filtered by one or more criteria. The patients in the patient list have associated medical images that may be retrieved and viewed on one or more of workstations 110A-D. When a manual query or request is requested, the load balancer 108 receives the request and passes it to the super node. The super node then fetches images from the PACS 122 and propagates the images to all nodes in the cluster 124 through the same distribution process. In other examples, a node other than the super node may fetch the images from the PACS 122. The cluster 124 utilizes a peer-to-peer distribution system for images with information about each image stored in the super node as an index. The index comprises a directory of the images on the cluster 124 and which of the workstations contains the image. A node retrieving requesting an image may access the super node in the cluster 124 and obtain portions of the image from all the nodes in the cluster 124 according to the index.

In some examples, the system 100 may also include a second facility or network with second plurality of medical imaging devices, such as a second magnetic resonance imaging (MRI) machine 112, a second ultrasound imaging machine 114, and a second mammogram/tomosynthesis imaging machine 116. The second plurality of medical imaging devices may be connected to a second load balancer 118 and a second cluster 126 of workstations 120A-D. The communication between the PACS 122, the second cluster 126 of workstations 120A-D, the second load balancer 118, and the second plurality of medical imaging devices may be substantially the same as discussed above with respect to the first cluster 124. In some examples, the second load balancer 118 may be omitted, and the second cluster 126 may be in communication with the first load balancer 118 which may serve the second cluster 126 in a similar manner as to how the first load balancer 118 serves the first cluster 124.

Figure 1B:
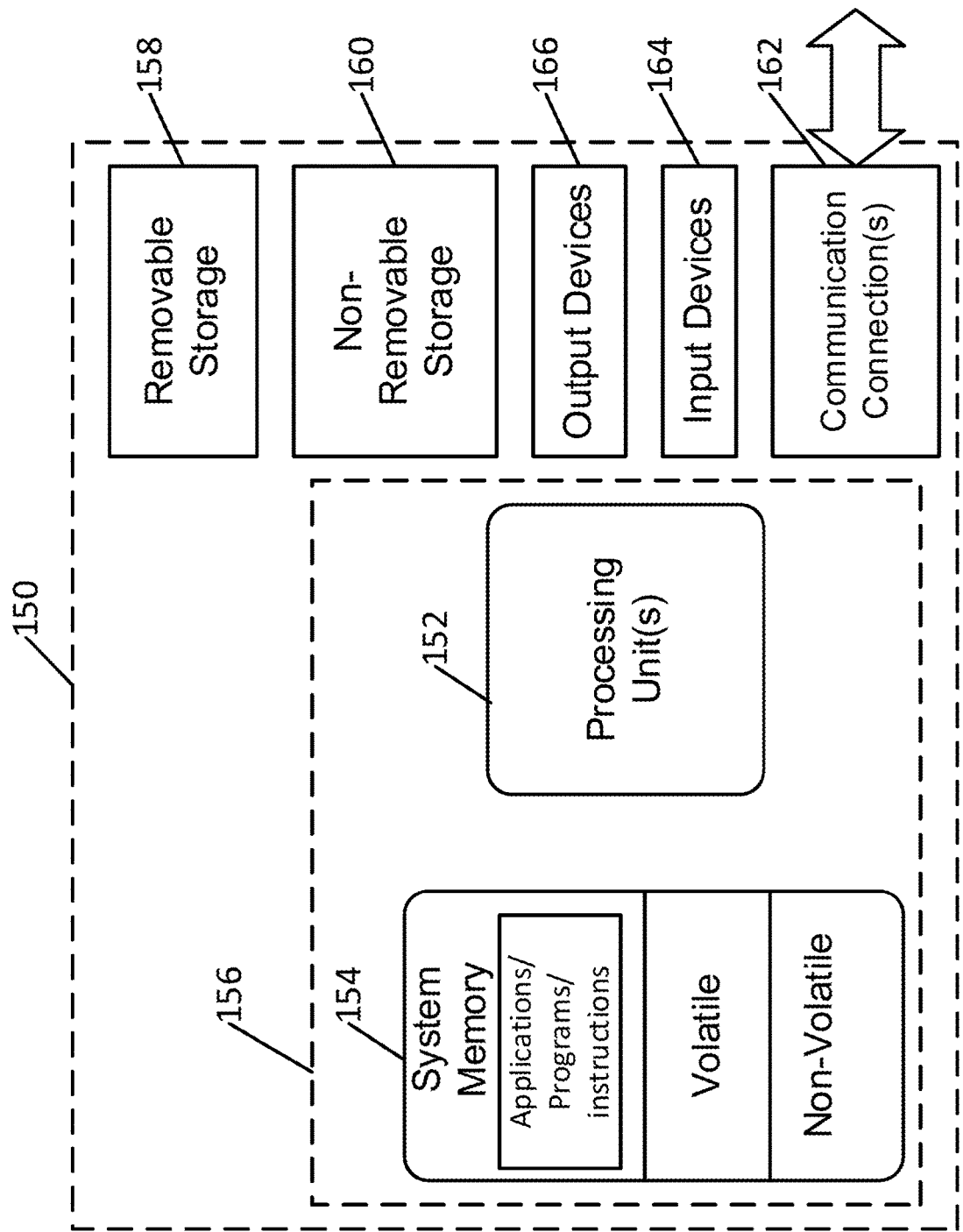
FIG. 1B depicts an example of a suitable operating environment for incorporation into the system of FIG. 1A.

FIG. 1B depicts an example of a suitable operating environment for incorporation into the system 100 of FIG. 1A. For example, the operating environment may be suitable for incorporation and use with the workstations of system 100. In its most basic configuration, operating environment 150 typically includes at least one processing unit 152 and memory 154. Depending on the exact configuration and type of computing device, memory 154 (storing instructions to perform the active monitoring embodiments disclosed herein) may be volatile (such as RAM), non-volatile (such as ROM, flash memory, etc.), or some combination of the two. This most basic configuration is illustrated in FIG. 1B by dashed line 156. Further, environment 150 may also include storage devices (removable 158, and/or non-removable 160) including, but not limited to, solid-state storage, magnetic or optical disks or tape. Similarly, environment 150 may also have input device(s) 164 such as keyboard, mouse, pen, voice input, touch input, etc. and/or output device(s) 166 such as a display, speakers, printer, etc. For example, the environment 150 may include a touchscreen that allows for both display and input. The input devices 164 may also include one or more antennas to detect signals emitted from the various the performance tracking devices 102. Also included in the environment may be one or more communication connections 162, such as LAN, WAN, point to point, WIFI, BLUETOOTH, TCP/IP, etc. In embodiments, the connections may be operable to facilitate point-to-point communications, connection-oriented communications, connectionless communications, etc.

Operating environment 150 typically includes at least some form of computer readable media. Computer readable media can be any available media that can be accessed by processing unit 152 or other devices comprising the operating environment. By way of example, and not limitation, computer readable media may comprise computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transitory medium that can be used to store the desired information. Computer storage media does not include communication media. Computer storage media may be referred to as computer storage devices.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, microwave, and other wireless media. Combinations of the any of the above should also be included within the scope of computer readable media.

The operating environment 150 may be a single computer operating in a networked environment using logical connections to one or more remote computers. The remote computer may be a personal computer, a server, a router, a network PC, a peer device or other common network node, and typically includes many or all of the elements described above as well as others not so mentioned. The logical connections may include any method supported by available communications media.

Figure 2A:
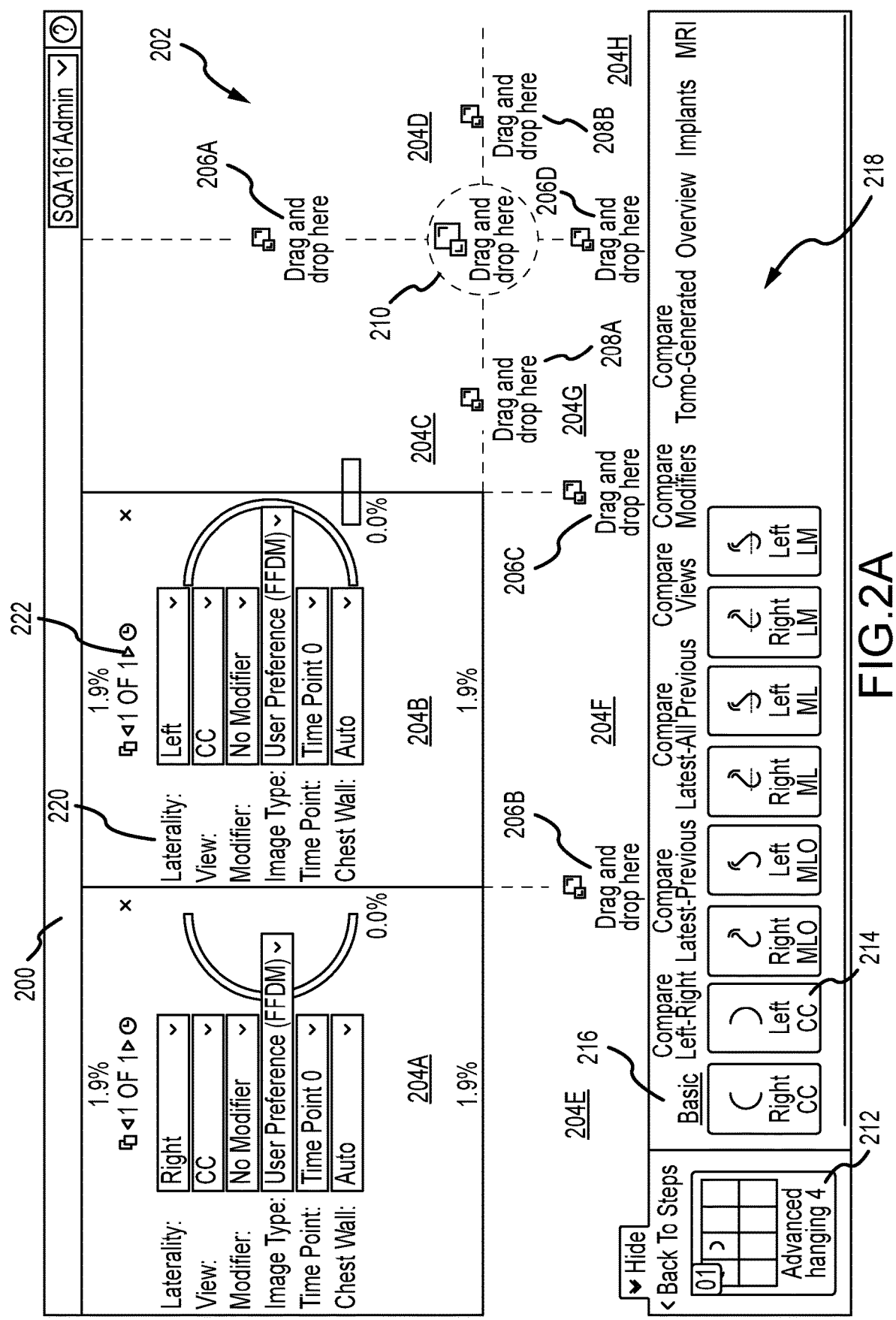
FIG. 2A depicts an example user interface for creating a multimodality hanging protocol.

FIG. 2A depicts an example user interface 200 for creating a multimodality hanging protocol. The user interface 200 includes a workspace 202 having a plurality of viewports 204A-H. The workspace 202 is split into a plurality of segments, and in the present example, the workspace is split into eight segments, or octants, with each octant being a separate viewport 204A-H. Each of the viewports 204A-H may also be referred to herein as tiles. The user interface 200 also includes an editor bar 218 with a plurality of building blocks 214 and a display of the current hanging step 212. The display of the current hanging step 212 shows a miniature live view of the workspace 202 for the particular hanging step. The display of the current hanging step 212 also indicates the number of the hanging step. For example, the display of the current hanging step 212 displayed indicates in the upper left-hand corner that it is the first hanging step in the hanging protocol with the number "01." If the "Back to Steps" option above the display of the current hanging step 212 is selected, the editor bar 218 displays a sequence of hanging steps that may be edited. A particular hanging step from the sequence of hanging steps may then be selected for further editing.

The building blocks 214 represent medical images that will be displayed for a patient. In general, the building block 214 is associated with a modality and a view. For instance, the building block "Left CC" is an x-ray image, such a mammography or tomosynthesis image, of the left breast taken at the cranio-caudal (CC) view. In contrast, the "Right MLO" building block is an x-ray image, such as a mammography or tomosynthesis image, of the right breast taken at the medio-lateral oblique view. While not shown in FIG. 2A, other building blocks 214 for other modalities, such as MRI, CT, PET, and/or ultrasound, may also be displayed for use. Additional building blocks may also be accessed by selecting a different building block category option 216. In addition, in some examples, the hanging protocol may be specific to medical images of breasts. In other examples, the hanging protocol may relate to other portions of the body and the building blocks may be specific to that portion of the body.

The building blocks can be dragged and dropped into the workspace 202 to fill the viewports. As depicted in FIG. 2A, viewport 204A and viewport 204B have already been filled with building blocks 214. In particular, viewport 204A has been filled with the "Right CC" building block and viewport 204B has been filled with the "Left CC" building block. The remaining viewports 204C-H are empty and may receive a building block.

In the viewports 204A-B that have already been filled with building blocks 214, a menu of options 220 is displayed for further configuration of the building block 214 in the particular viewport. The menu of options 220 may include options for laterality (i.e., left or right breast), view, modifiers, image type, time point (e.g., current or a number of prior images), and chest wall location (i.e., is the chest wall on the left or right side of the image). Each option may be modified through the use of a drop down menu or similar menus. The options may also be set to "User Preference," which is the example option displayed for "Image Type" in FIG. 2A. By setting an option to "User Preference" the image that is imported will be displayed according to the particular user preferences of the radiologist accessing images according to the customized hanging protocol. For instance, a first radiologist may generate the hanging protocol and share it with a second radiologist. Each radiologist may have stored user preferences that differ from those of other radiologists. As such, the hanging protocol may still be used by the second radiologist, but the user preferences of the second radiologist will be applied rather than the personal preferences of the first radiologist. Layer options 222 may also be displayed in a filled viewport, such as viewports 204A-B. By selecting the arrows in the layer option 222, current or prior images may be selected for display. The layers may also include other views or images that that are not related by time points, such as equivalent or modified views.

The viewports 204A-H are visually separated with dashed separation lines of a smart grid. The vertical separation lines (which separate columns) may include a column hotspot 206A-D. The column hotspots 206A-D allow for an automatic expansion of a building block 214 into two columns when the building block 214 is dragged onto one of the column hotspots 206A-D. For instance, if the building block 214 is dropped on the column hotspot 206A, the building block 214 fills both viewport 204C and viewport 204D. The horizontal separation lines (which separate rows) may include a row hotspot 208A-B. The row hotspots 208A-B allow for an automatic expansion of a building block 214 into two rows when the building block 214 is dragged onto one of the row hotspots 208A-B. For instance, if the building block 214 is dragged onto hotspot 208A, the building block 214 fills both viewport 204C and viewport 204G. At the intersection of the vertical and horizontal separation lines, a quadrant hotspot 210 may be displayed. The quadruple hotspot 210 allows for an automatic expansion of a building block 214 into the four viewports surrounding the quadruple hotspot 210. For instance, if building block 214 was dragged on to the quadruple hotspot 210, the building block fills viewports 204C-D and viewports 204G-H. The hotspots allow for more efficient, quick, customizable and intuitive way of resizing and filling of building blocks 214 into the workspace 202. The hotspot functionality allows for the user to quickly fill the building blocks in the hanging protocols just in the way that the user would prefer. The quadruple hotspot 210 may also be referred to as a single tile hotpot.

Some categories of building blocks, such as "Compare Left-Right," may include composite building blocks that fill more than one viewport. The composite building blocks are effectively a combination of multiple individual building blocks. An example composite building block may be a "Right CC" building block and a "Left CC" building block paired together. Such a composite building block is two columns wide and one row high. As such, if the composite building block is dragged into viewport 204E, it fills viewports 204E-204F. Additional sizes and configurations of composite building blocks are also contemplated, such as: one row by three columns; one row by four columns; two rows by one column; two rows by two columns; two rows by three columns; two rows by four columns; and so on. Composite building blocks may also be composed of a combination of individual building blocks of different imaging modalities.

Figure 2B:
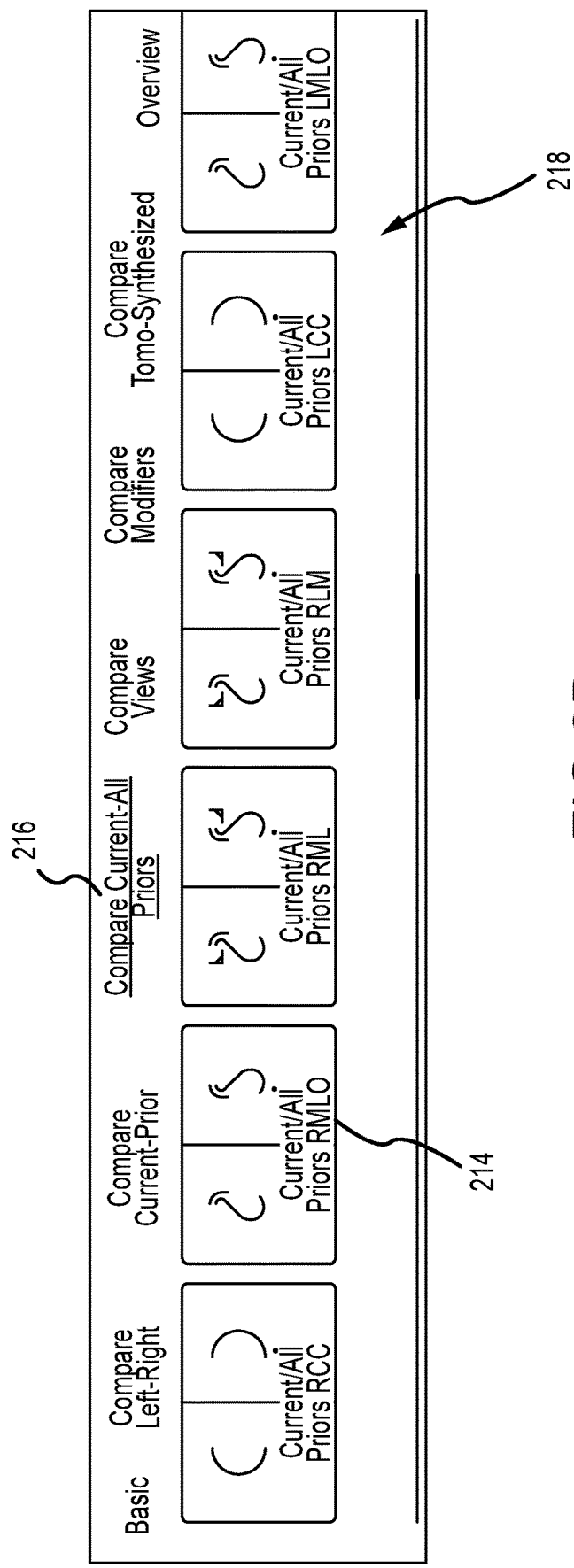
FIG. 2B depicts another example of an editor bar within the example user interface.

FIG. 2B depicts another example of the editor bar 218 with the "Compare Current-All Priors" category option 216 selected. With the "Compare Current-All Priors" category option 216 selected, the editor bar 218 is populated with composite building blocks 214 that have a dimension of one row by two columns. For example, one composite building block 214 is "Current/All Priors RCC." That building block includes the current right breast CC image and all the prior right breast CC images in a stack displayed adjacent the current right breast CC image. Stacked images are discussed in further detail below with respect to FIG. 2F.

Figure 2C:
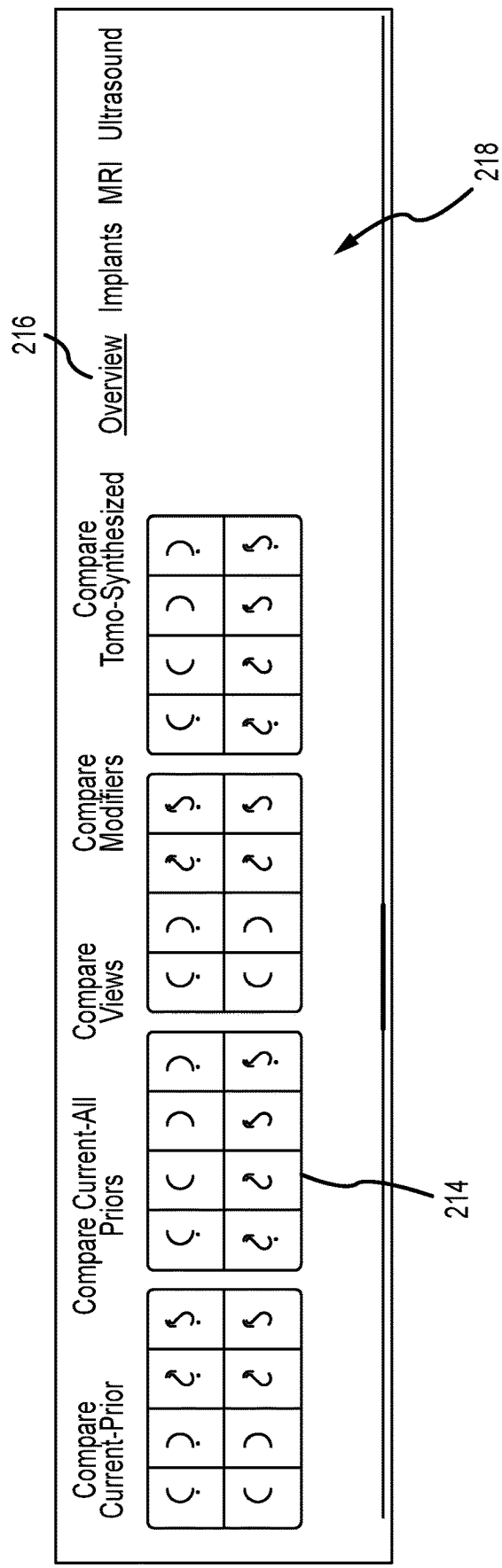
FIG. 2C depicts another example of an editor bar within the example user interface.

FIG. 2C depicts another example of the editor bar with the "Overview" category option 216 selected. With the "Overview" category option 216 selected, the editor bar 218 is populated with composite building blocks 214 that have a dimension of two rows by four columns. Each of the composite building blocks 214 in the "Overview" category are intended to fill the entire workspace 202. The composite building blocks 214 include individual building blocks arranged so as to provide a desired overview of the breast images.

Figure 2D:
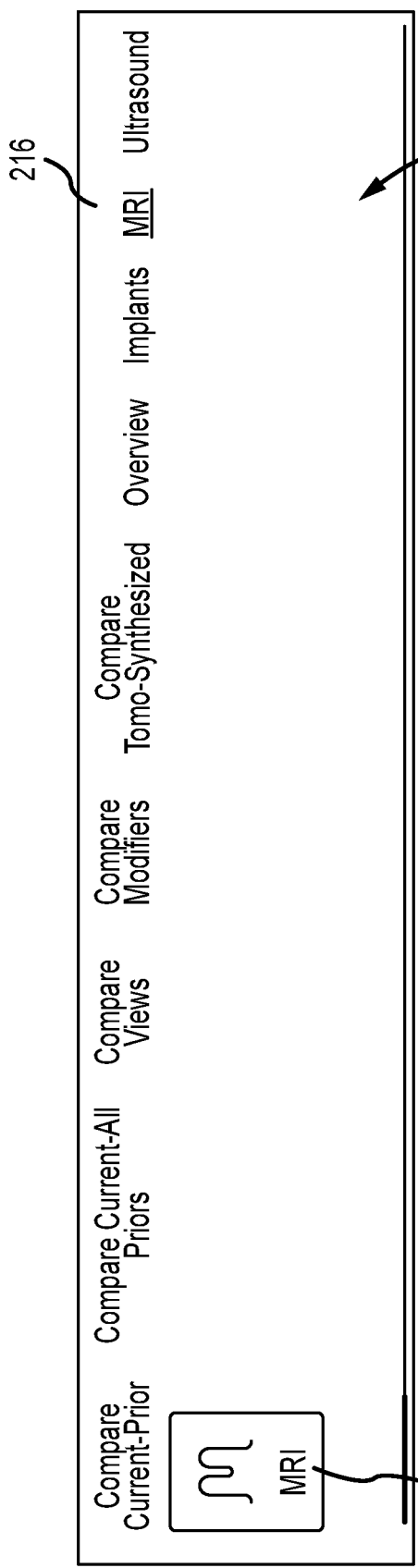
FIG. 2D depicts another example of an editor bar within the example user interface.
Figure 2E:
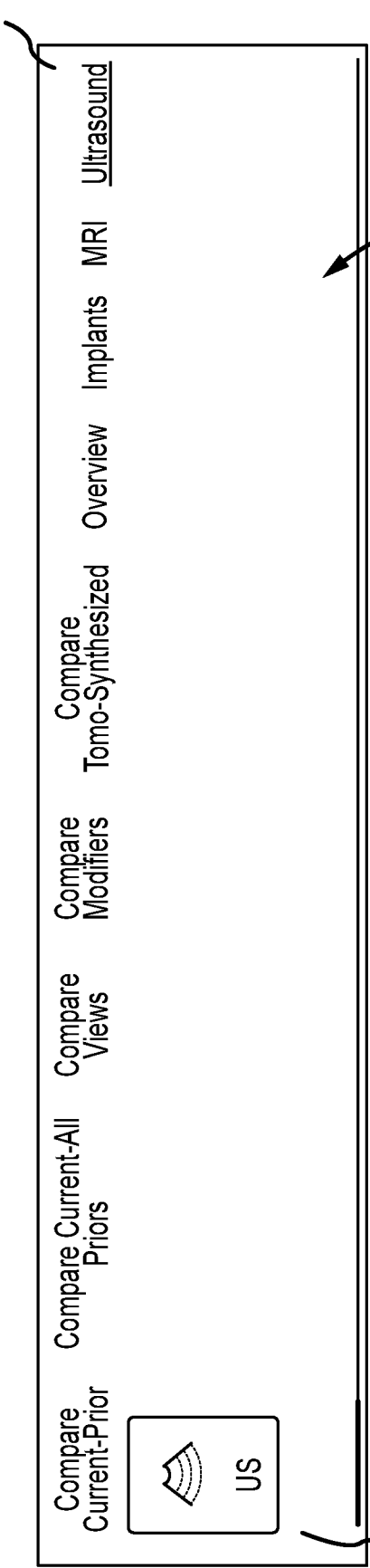
FIG. 2E depicts another example of an editor bar within the example user interface.

FIG. 2D depicts another example of the editor bar 218 with the "MRI" category option 216 selected. With the "MRI" category option 216 selected, the editor bar 218 is populated with building blocks 214 related to MRI images. FIG. 2E depicts another example of the editor bar 218 with the "Ultrasound" category option 216 selected. With the "Ultrasound" category option 216 selected, the editor bar 218 is populated with building blocks 214 related to ultrasound images.

Figure 2F:
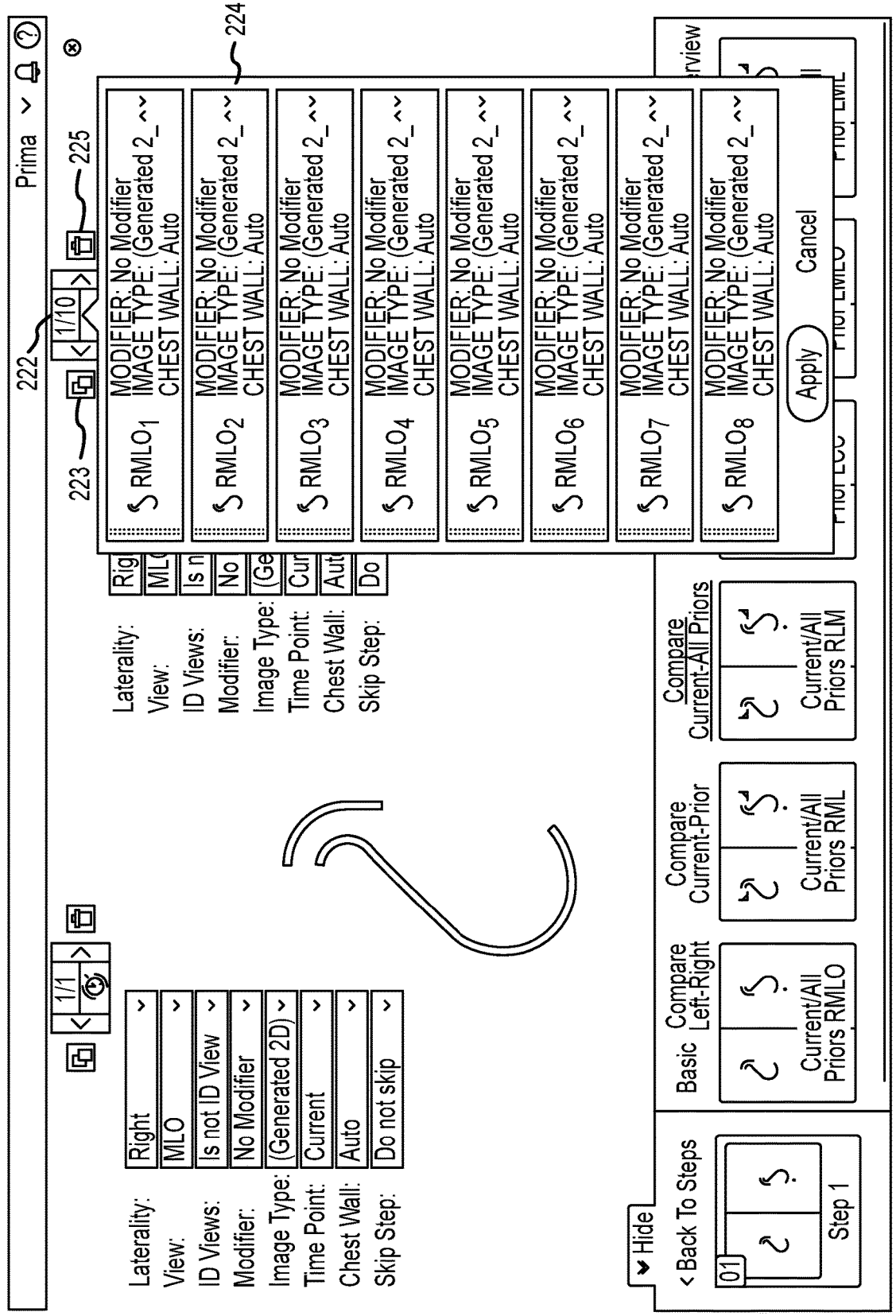
FIG. 2F depicts another example user interface for creating a multimodality hanging protocol with a building block having stacked layers.

FIG. 2F another example user interface 200 for creating a multimodality hanging protocol with a stacked building block in a viewport. When a building block is added to the workspace, that building block may include additional prior layers. For example, a "Left CC" building block may also be configured to include prior CC images of left breast. The prior images included with the building block are stacked such that one medical image for the patient will be displayed in the respective viewport, and the prior images can be scrolled or stepped through via user interaction. The order and number of prior images that are to be stacked according to the hanging protocol can be configured through the user interface features depicted in FIG. 2F. For example, by selecting the layer option 222, a drop down layer ordering menu 224 may be displayed. The layer ordering menu 224 provides a list of the view or images that are stacked in the current viewport or building block. Each view or image in the list includes a numerical indicator that indicates a relative to one another. For instance, the image "RMLO1" was taken more recently than the image "RMLO2." The ordering of the images may be altered by the user creating/editing the hanging protocol. The image ordering may be altered by using the up or down arrows shown next to each image or the images can be dragged and dropped in a new order. When actual medical images are imported according to the hanging protocol, they will be stacked according to the order set in the ordering menu 224. The user may then click through or scroll through the images. Images other than prior images may also be stacked. For example, modified or equivalent views may also be added to the stack. Adding additional images to the stack may be accomplished by selecting the add layer option 223. Accordingly, even where a building block may not initially include stacked views or images, layers corresponding to different views or images can be added to create a stack by selecting the add layer option 223. In some examples, layers may be added to the stack by dragging additional building blocks onto a filled viewport. Layers may also be deleted through the selection of a delete layer option 225. In some examples, the delete layer option 225 may also be used to remove the building block that fills the viewport.

FIG. 3A depicts an example user interface 300 for creating a multimodality hanging protocol with a composite building block 314. The user interface 300 is substantially similar to the user interface 200 discussed above with reference to FIG. 2A and may be displayed when a composite building block of one row by two columns is selected. For instance, user interface 300 includes a workspace 302 that includes a plurality of viewports 304A-H. The workspace 302 also includes two quadruple hotspots 310A-B. The workspace 302, however, also includes an octuple hotspot 330. The octuple hotspot 330 allows for an automatic expansion of the composite building block into all eight viewports 304A-H. The octuple hotspot 330 may also be referred to as a double tile hotspot.

Figure 3B:
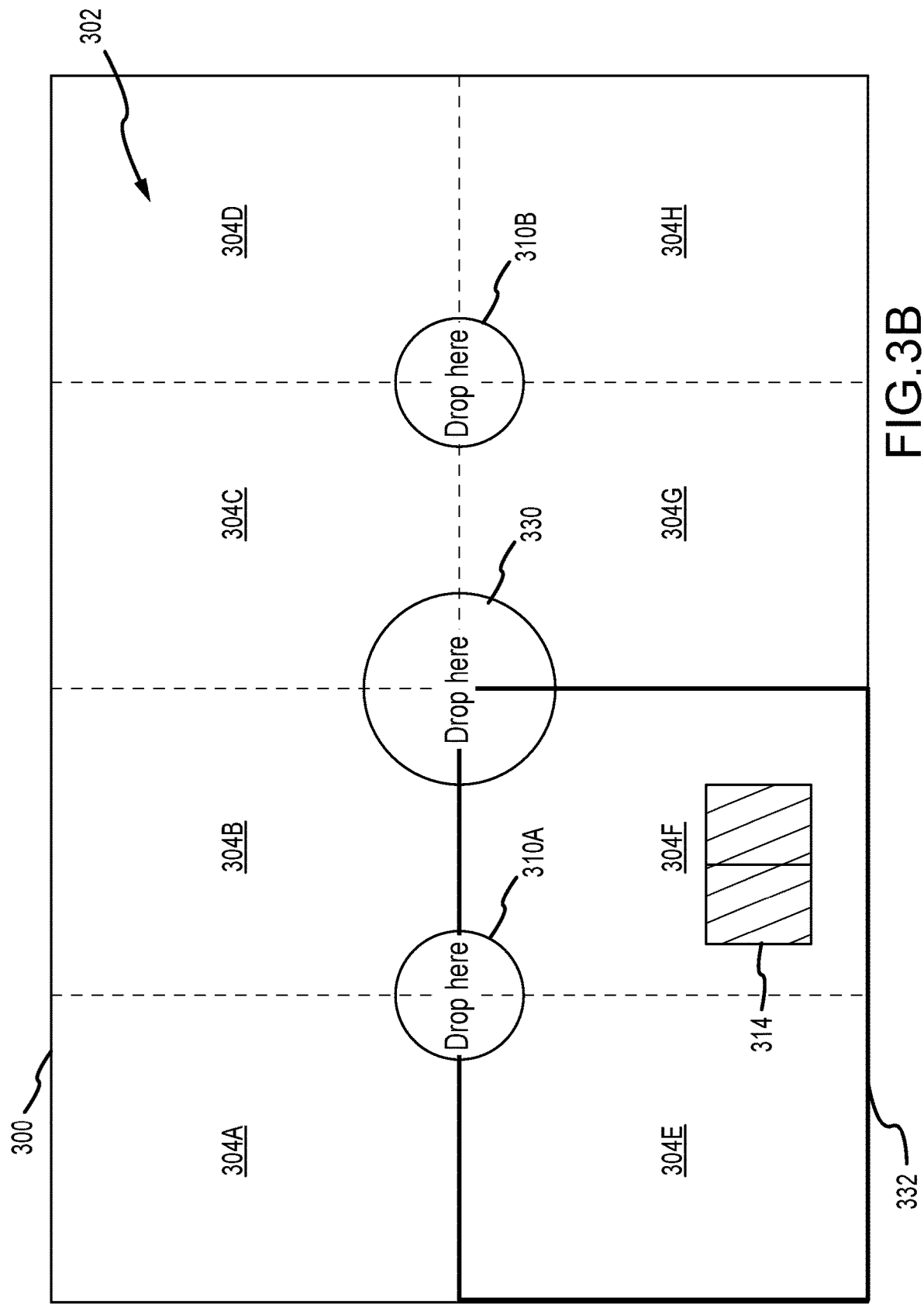
FIG. 3B depicts the example user interface of FIG. 3A with the composite building block being dragged onto the workspace.

FIG. 3B depicts the example user interface 300 of FIG. 3A with the composite building block 314 being dragged onto the workspace 302. When the composite building block 314 is dragged onto the workspace 302, a drop zone outline 332 is displayed to indicate which of the viewports 304A-H will be filled with the composite building block 314. The drop zone outline 332 may be a color indicator, a bolding of the borders of the viewports that will be filled, or any other highlighting or indicator that indicates which viewports will be filled by the composite building block. In the example depicted in FIG. 3B, the composite building block 314 has been dragged over viewport 304F. Because the composite building block 314 is one row high and two columns wide, the drop zone outline 332 indicates that both viewport 304E and viewport 304F will be filled by the composite building block 314.

Figure 3C:
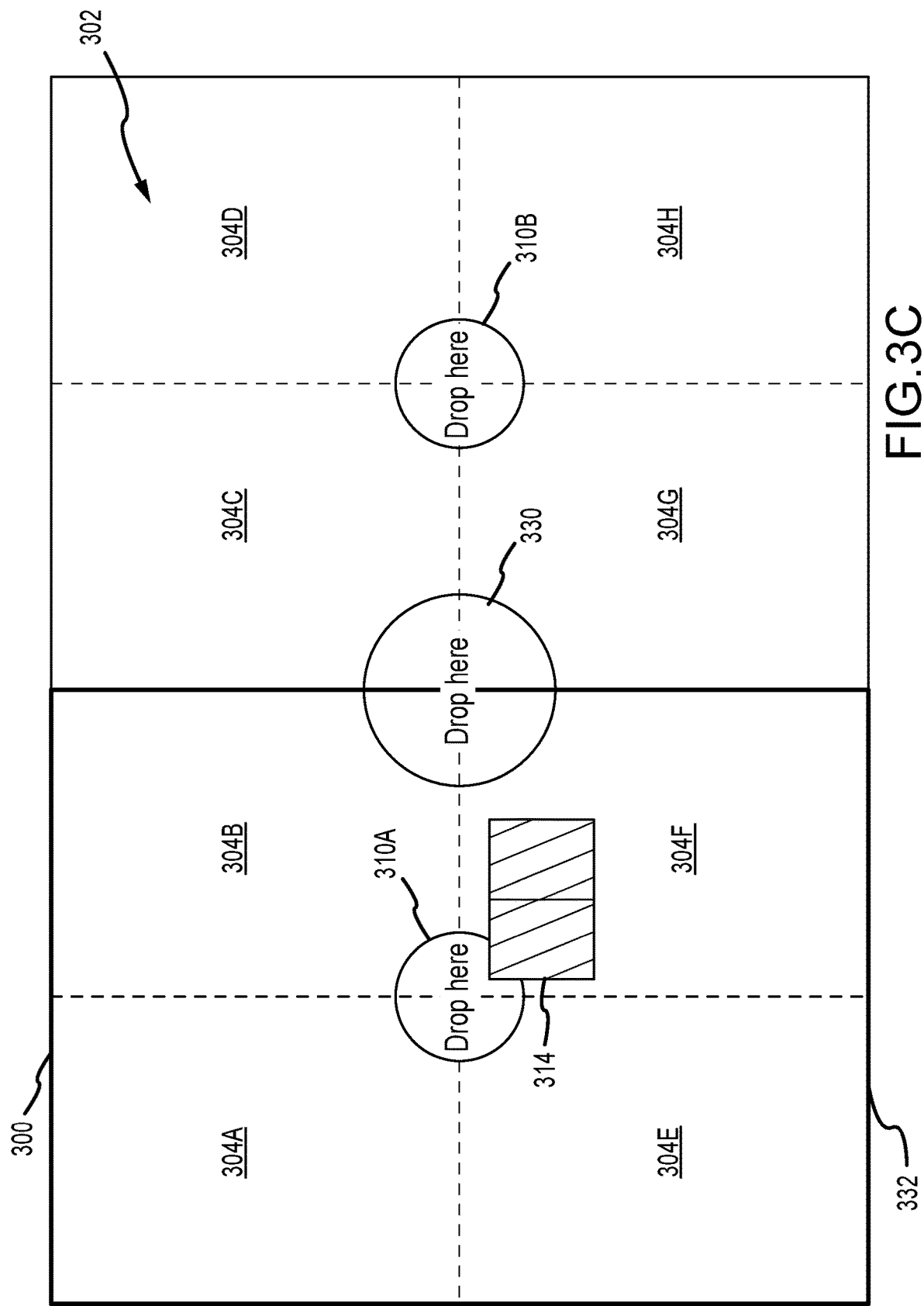
FIG. 3C depicts the example user interface of FIG. 3A with the composite building block being dragged onto the quadruple hotspot.

FIG. 3C depicts the example user interface 300 of FIG. 3A with the composite building block 314 being dragged onto the quadruple hotspot 310A. When the composite building block 314 is dragged onto the quadruple hotspot 310A, the drop zone outline 332 updates to show that viewports 304A-F will be filled if the composite building block 314 is dropped in that location.

Figure 3D:
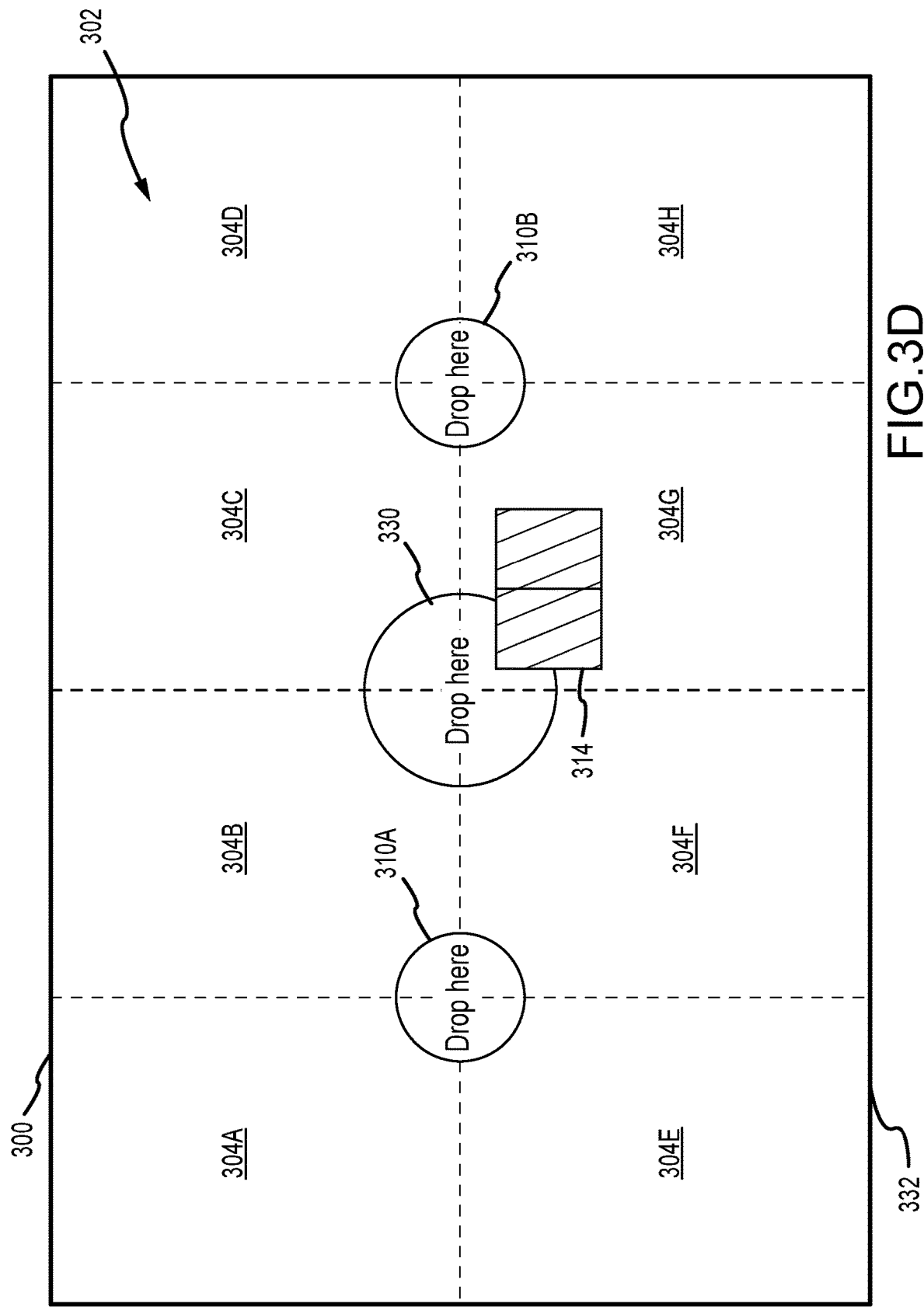
FIG. 3D depicts the example user interface of FIG. 3A with the composite building block being dragged onto the octuple hotspot.

FIG. 3D depicts the example user interface 300 of FIG. 3A with the composite building block 314 being dragged onto the octuple hotspot 330. When the composite building block 314 is dragged onto the octuple hotspot 330, the drop zone outline 332 updates to show that all the viewports (i.e., viewports 304A-H) will be filled if the composite building block 314 is dropped in that location.

Figure 4A:
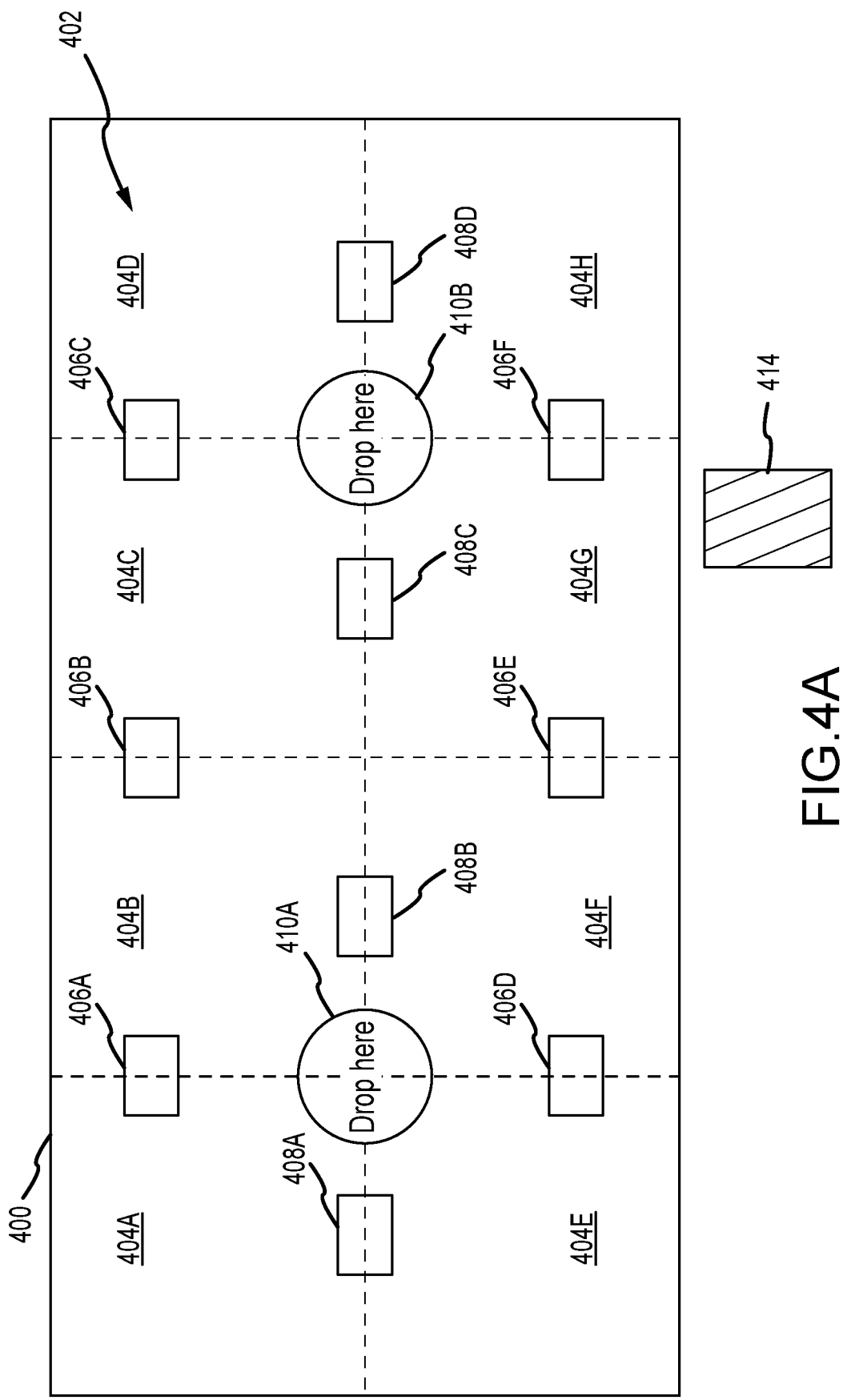
FIG. 4A depicts an example user interface for creating a multimodality hanging protocol with a building block.

FIG. 4A depicts an example user interface 400 for creating a multimodality hanging protocol with a building block 414. The user interface 400 is substantially similar to the user interface 200 depicted in FIG. 2A, with the exception that all the viewports 404A-H are empty in user interface 400. Like the user interface 200 in FIG. 2A, the user interface 400 includes a workspace 402 which has a plurality of column hotspots 406A-F, a plurality of row hotspots 408A-D and a plurality of quadruple hotspots 410A-B.

Figure 4B:
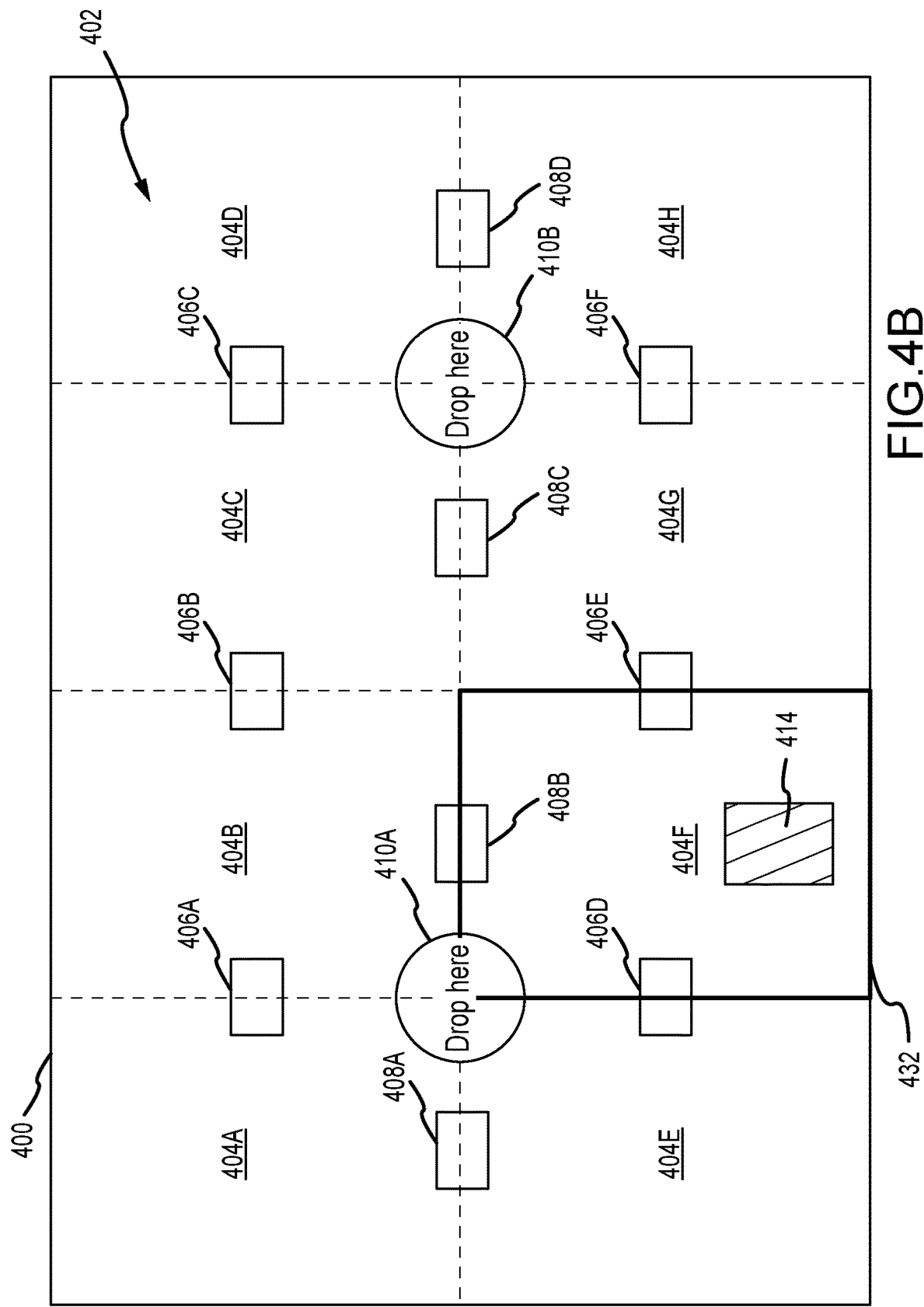
FIG. 4B depicts the example user interface of FIG. 4A with the building block being dragged onto the workspace.

FIG. 4B depicts the example user interface 400 of FIG. 4A with the building block 414 being dragged onto the workspace 402. When the building block 414 is dragged onto the workspace 402, a drop zone outline 432 is displayed to indicate which of the viewports 404A-H will be filled with the composite building block 414. In the example depicted in FIG. 4B, the building block 414 has been dragged over viewport 404F. Because the building block 414 is one row high and one column wide, the drop zone outline 432 indicates that only viewport 404F will be filled by the building block 414.

Figure 4C:
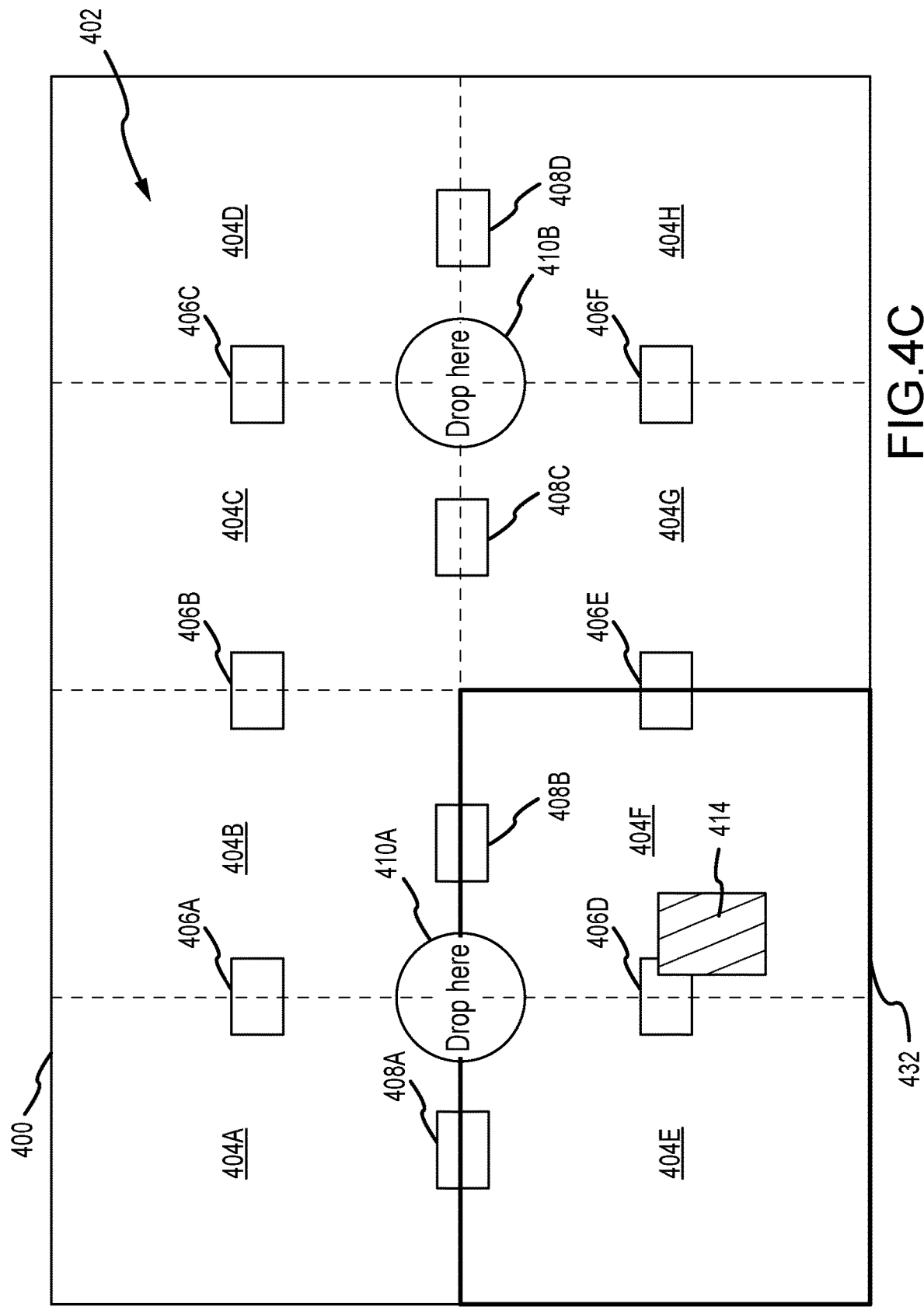
FIG. 4C depicts the example user interface of FIG. 4A with the building block being dragged onto the column hotspot.

FIG. 4C depicts the example user interface 400 of FIG. 4A with the building block 414 being dragged onto the column hotspot 406D. When the building block 414 is dragged onto the column hotspot 406D, the drop zone outline 432 updates to show that the viewports 404E-F will be filled by the building block 414 if the building block 414 is dropped at that location.

Figure 4D:
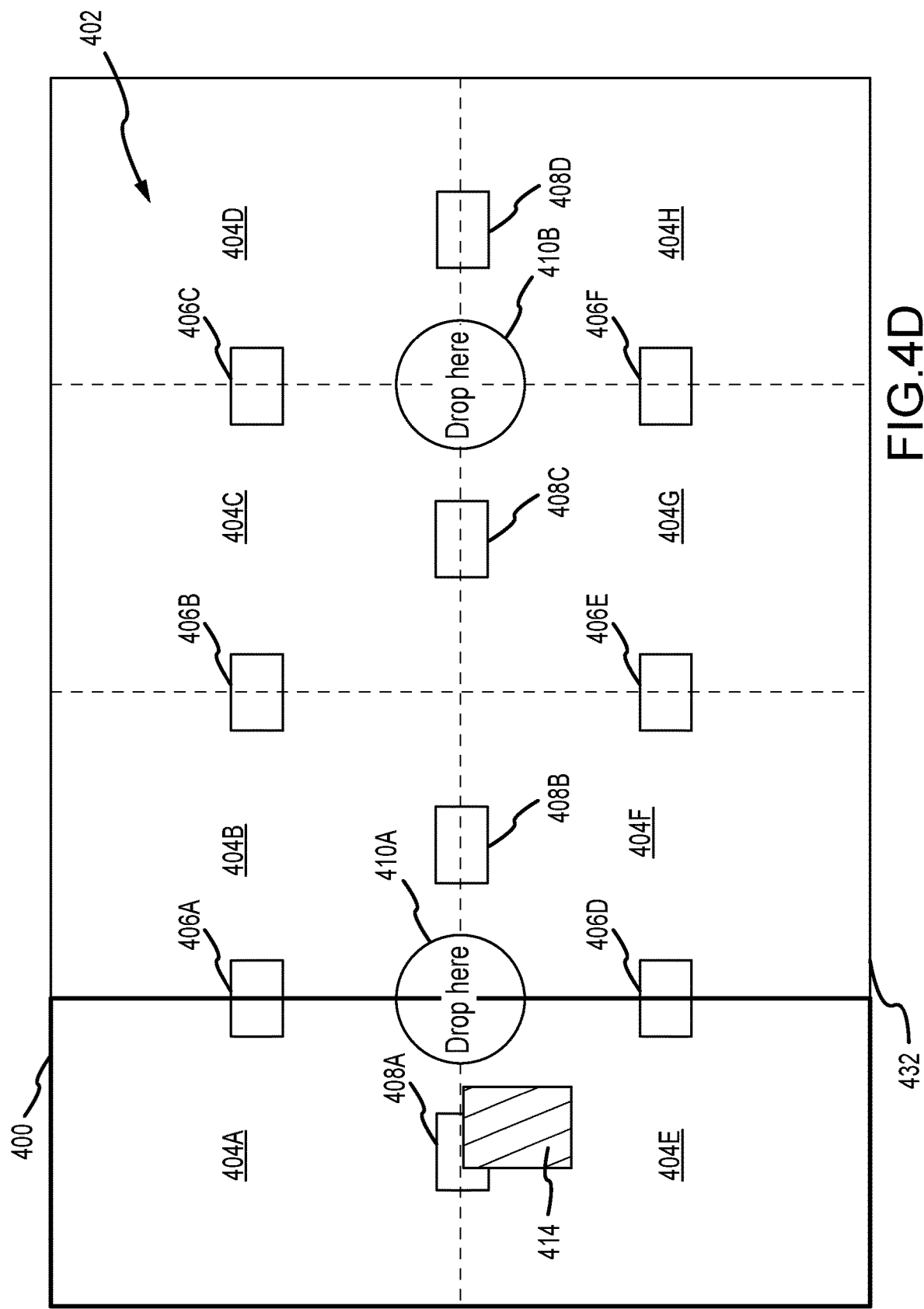
FIG. 4D depicts the example user interface of FIG. 4A with the building block being dragged onto the row hotspot.

FIG. 4D depicts the example user interface 400 of FIG. 4A with the building block 414 being dragged onto the row hotspot 408A. When the building block 414 is dragged onto the row hotspot 408a, the drop zone outline 432 updates to show that the viewport 404A and the viewport 404E will be filled by the building block 414 if the building block 414 is dropped at that location.

Figure 4E:
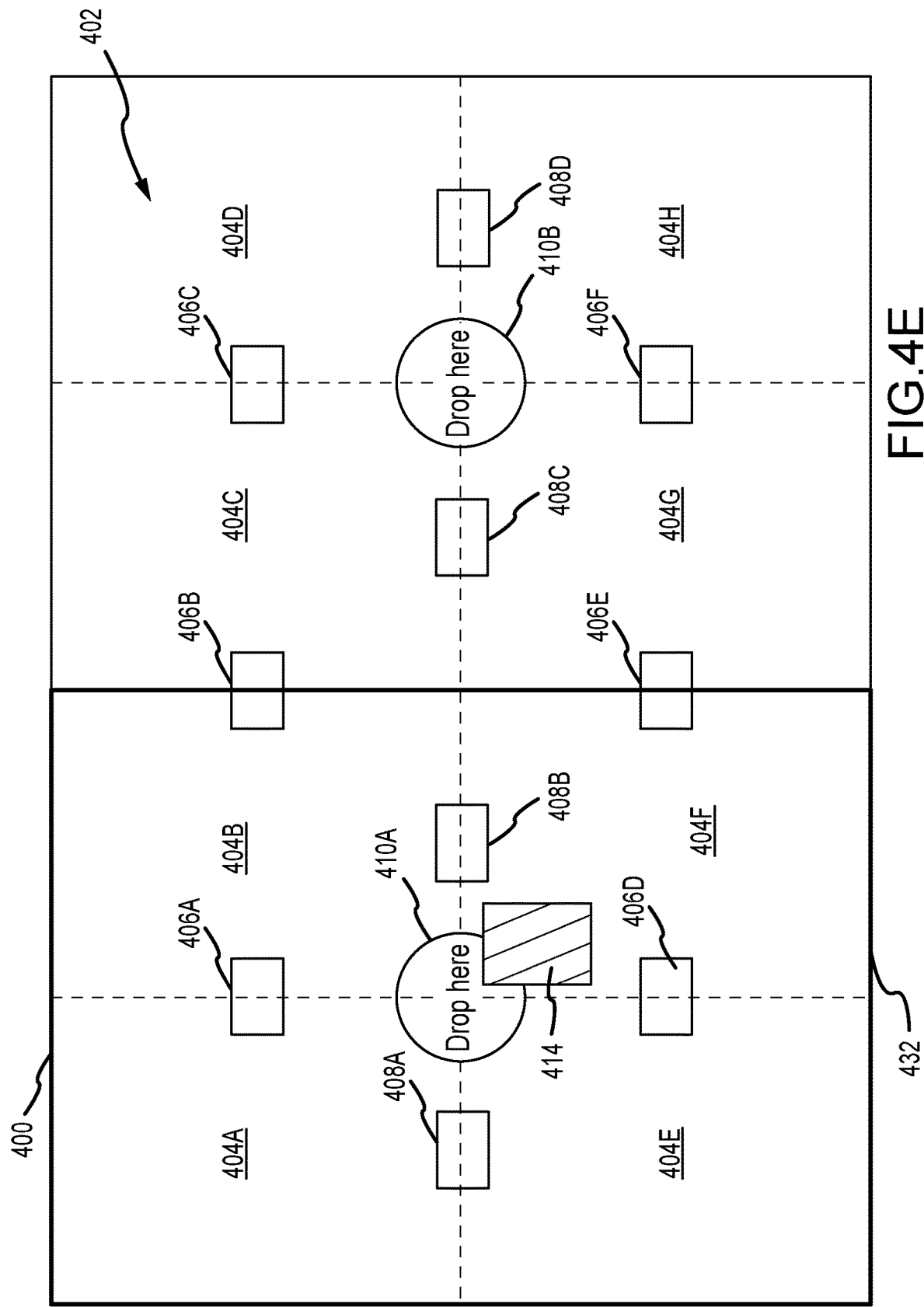
FIG. 4E depicts the examples user interface of FIG. 4A with the building block being dragged onto the quadruple hotspot.

FIG. 4E depicts the examples user interface 400 of FIG. 4A with the building block 414 being dragged onto the quadruple hotspot 410A. When the building block 414 is dragged onto the quadruple hotspot 410A, the drop zone outline 432 updates to show that the viewports 404A-B and the viewports 404E-F will be filled by the building block 414.

Different workspaces may be displayed depending on the type of building block that is selected from the editor bar. For instance, the workspace displayed in the user interface may dynamically update based on the type of building block that is selected to be added to the hanging protocol. As an example, when a one row by one column building block (such as building block 414) is selected, the workspace 400 depicted in FIG. 4A may be displayed. In contrast, when a one row by two column composite building block (such as building block 314) is selected, the workspace 300 depicted in FIG. 3A may be displayed. The different workspaces include different hotspots that are specific to the type or size of the building block. As such, the user is provided with additional dynamic information as to where the building block may be placed.

Figure 5A:
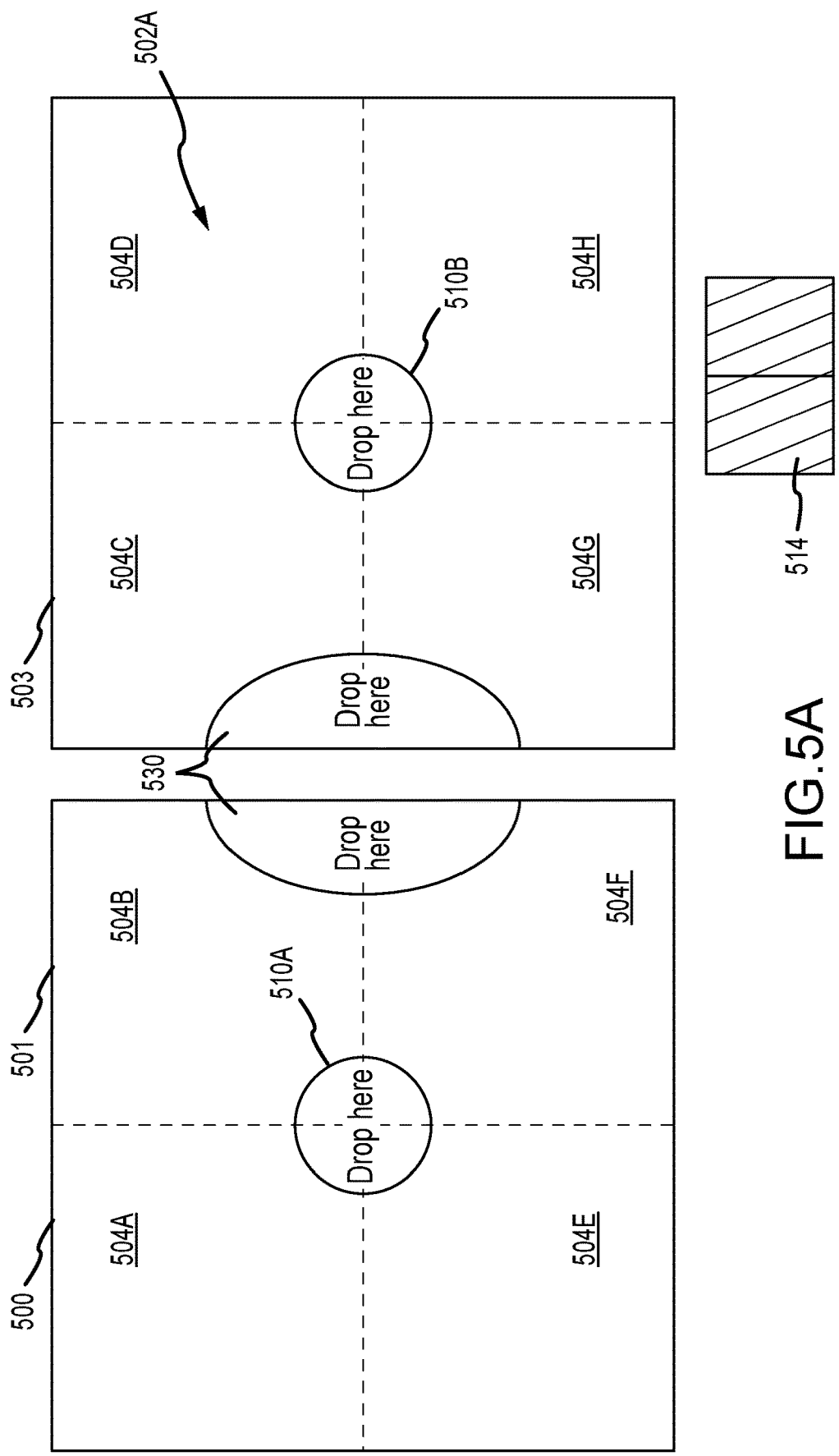
FIG. 5A depicts an example user interface for creating a hanging protocol that extends across a first display screen and a second display screen.

Hanging protocols may also be generated for multiple monitors or display screens. FIG. 5A depicts an example user interface 500 for creating a hanging protocol that extends across a first display screen 501 and a second display screen 503. The first display screen 501 and the second display screen 503 may be physically separate screens, or they may be virtual display screens such that a hanging protocol for two screens can be configured from a single screen. The user interface 500 is substantially similar to the user interface 300 depicted in FIG. 3A. For instance, the user interface 500 includes workspace 502A that has a plurality of viewports 504A-H, two quadruple hotspots 510A-B, and an octuple hotspot 530. The octuple hotspot 530, however, is split over the two different display screens. The workspace 502A is most often used when a composite building block, such as composite building block 514, is selected.

Figure 5B:
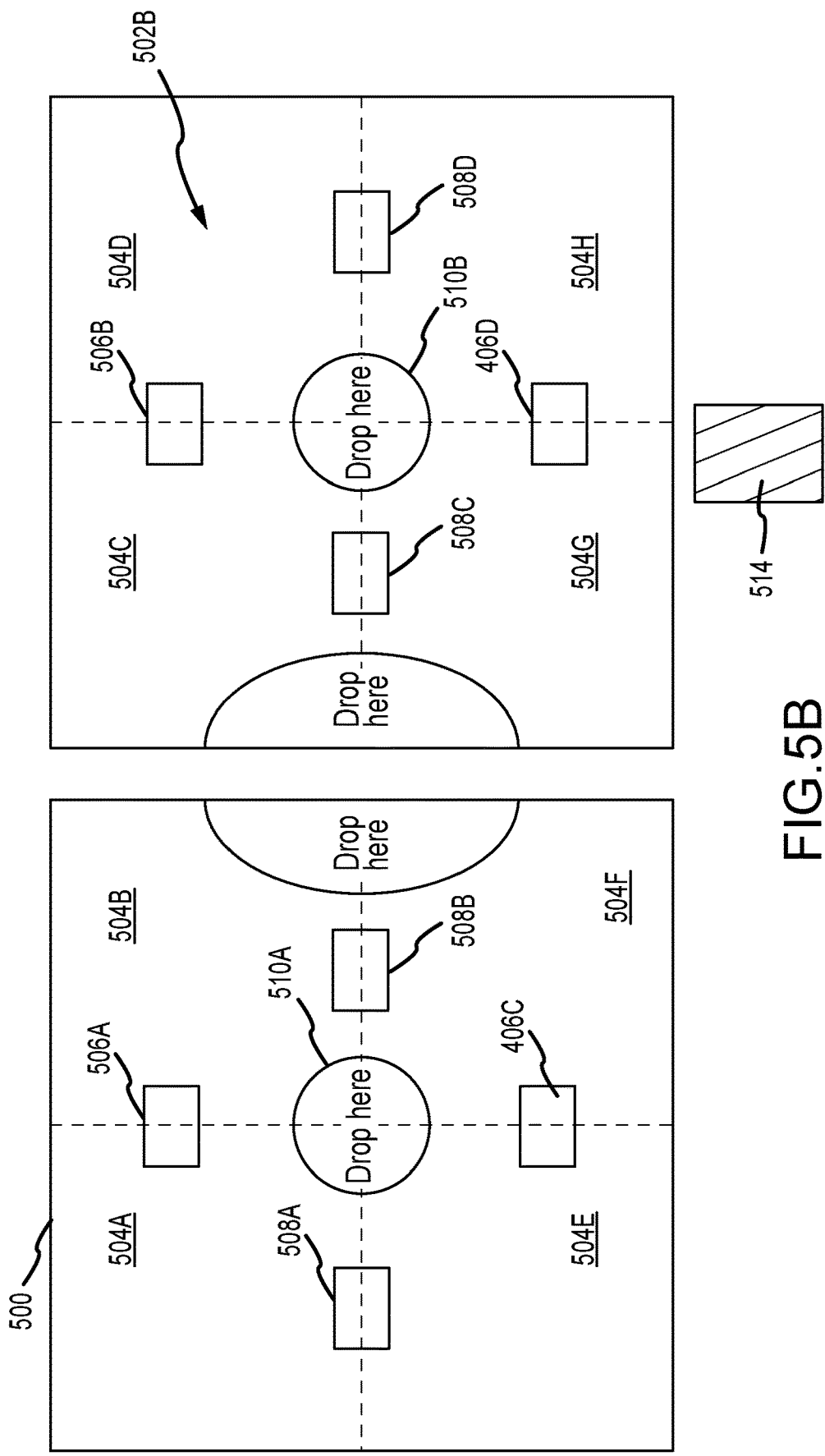
FIG. 5B depicts another example user interface for creating a hanging protocol that extends across a first display screen and a second display screen.

FIG. 5B depicts another example user interface 500 for creating a hanging protocol that extends across a first display screen 501 and a second display screen 503. The user interface 500 includes a workspace 502B that is most often used when a building block having a one row by one column dimension, such as building block 514, is selected. The workspace 502B includes a plurality of viewports 506A-H, two quadruple hotspots 510A-B, four column hotspots 506A-D, and four row hotspots 508A-D. The workspace 502B is similar to the workspace 400 depicted in FIG. 4A with exception that workspace 502B has been split between two display screens and the middle column hotspots and quadruple hotspot have been removed.

Figure 6:
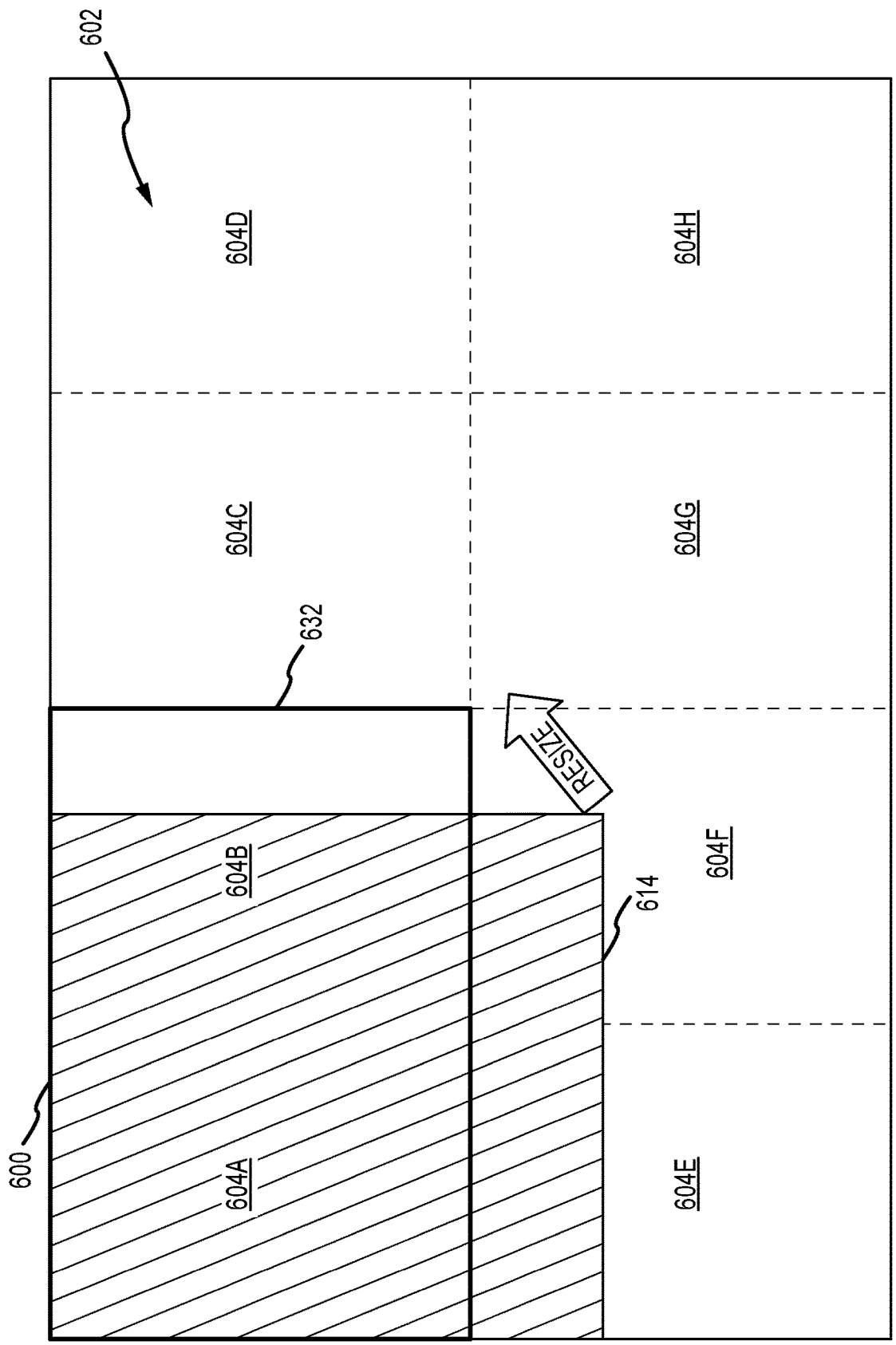
FIG. 6 depicts an example user interface for resizing a building block in generating a hanging protocol.

FIG. 6 depicts an example user interface 600 for resizing a building block 614 in generating a hanging protocol. Once a building block 614 has been placed into the workspace 602, it may be resized, and a drop zone outline 632 is displayed to show where the building block will be displayed. In the present example, the display of the building block 614 is constrained to fit the entirety of one or more of the viewports 604A-H. When the building block 614 is being resized (e.g., by dragging an edge or corner of the building block 614) as depicted in FIG. 6, a drop zone outline 632 is displayed to indicate the final size of the building block 614 if the user was to stop dragging the edge of the building block 614. That is, if the building block 614 was let go at the point depicted in FIG. 6, the building block would snap to fill viewports 604A-B.

Figure 7A:
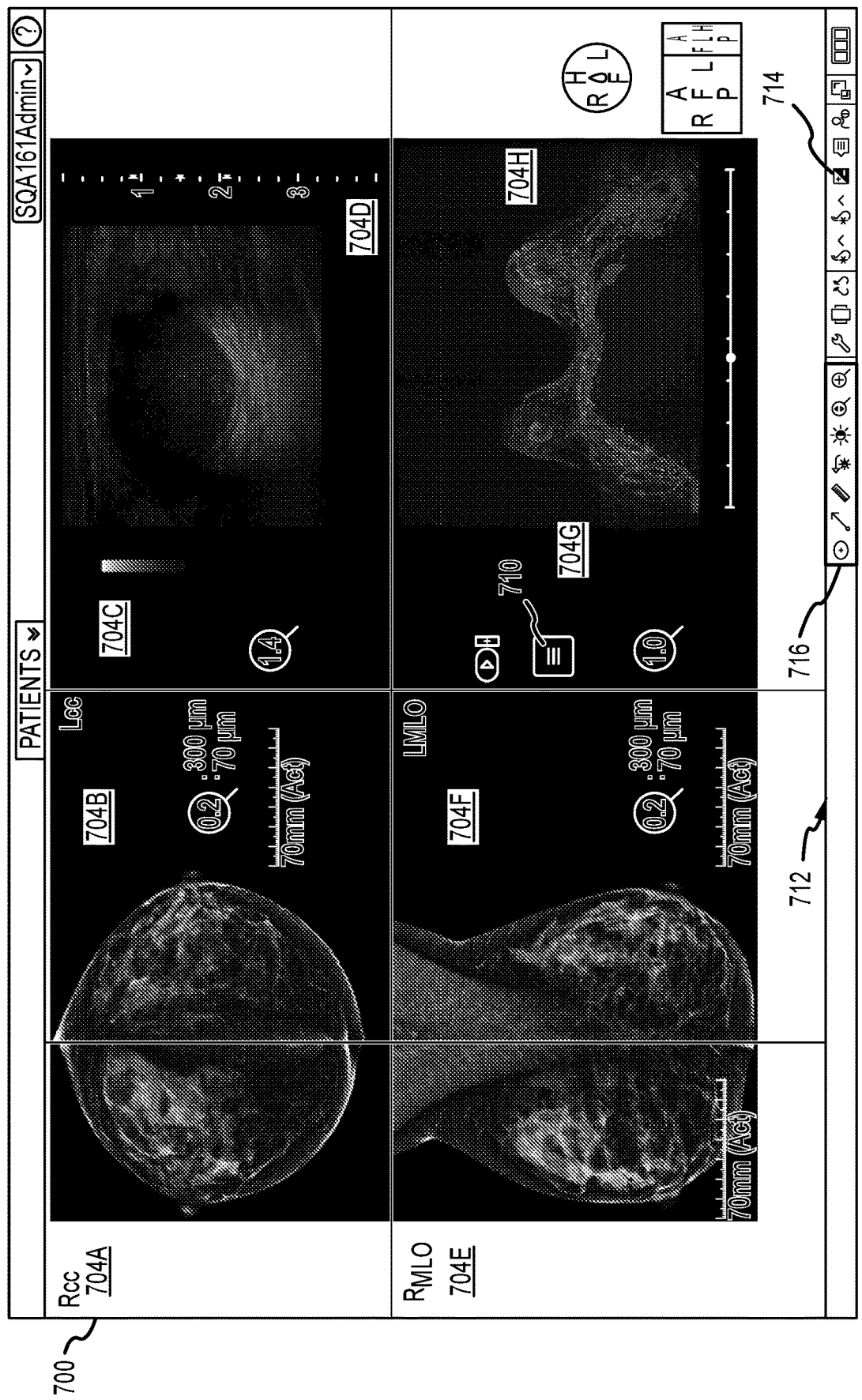
FIG. 7A depicts an example display of a hanging step of a hanging protocol populated with medical images of a patient.

FIG. 7A depicts an example display 700 of a hanging step of a hanging protocol populated with medical images of a patient. The display 700 resulted from a hanging protocol that had a Right CC building block in viewport 704A, a Left CC building block in viewport 704B, an ultrasound building block extending across viewports 704C-D, a Right MLO building block in viewport 704E, a Left MLO building block in viewport 704F, and an MRI building block extending across viewports 704G-H. As can be seen from FIG. 7, each of the viewports has been populated with the corresponding medical image. Different tools or options are shown in each viewport (or combination of viewports) showing the medical images, and at least a portion of those tools or options may be specific to the type of imaging modality used to capture the image. For example, for the MRI image extending across viewports 704G-H, an options icon 710 is displayed within the viewports 704G-H. The options icon 710, when selected, displays a set of options for modifying the displayed MRI image that are specific to the MRI imaging modality, such as colorization. The options icon 710 may also be moved or dragged to other locations within the display of the MRI image if desired. Other options icons 710 may be generated or placed over other displayed images. In such examples, the options associated with the respective options icons 710 are context sensitive in that the options will be based on the imaging modality for which the options icon is placed or associated.

Additional advantages may be achieved by having multiple modalities and context-sensitive tools and options being displayed concurrently on the same display. For instance, an abnormality that appears in on one imaging modality can now be more easily and efficiently be viewed on a second imaging modality concurrently and, optionally, even side-by-side, to help facilitate diagnoses and analysis by the radiologist. This is particularly helpful when the images from varying modalities are acquired at different times, thus, making more critical the potential need to see the same abnormality across different imaging modalities.

Additional options and tools are displayed within the lower toolbar or chrome 712. For example, when the tool icon 714 is selected, a plurality of tools will be displayed. Tools may include magnification, continuous zoom, ellipse, ruler, reset, and close study tools. With the plurality of tools displayed, each displayed tool may be dragged and dropped into the shortcut section 716 of the chrome 712. Once the tool has been dragged into the shortcut section 716, the tool is also then available in a secondary selection menu that is displayed when a user provides a secondary selection input, such as a right-click or a long press on a touch screen device. For example, a user may right-click anywhere on the display to generate the secondary selection menu. Other options and tools may also be dragged into the shortcut section 716 as well. The tools may also be dragged to other areas of the display to allow quick access to the tools in a certain location. As such, the tools for each radiologist may be customized by the radiologist herself. In addition, the ordering the tools may also be altered by the radiologist. The ordering of the tools may be altered by dragging and dropping the tools in the shortcut section 716. The altered ordering may also be reflected in the secondary selection menu. The tools that have been placed into the shortcut section 716 may be saved as personal preferences for the radiologist. By providing the customization features the radiologist does not need to navigate away from the images to find the proper tools to analyze the images. The customizations are also achieved without the need to visit other pages, such as a settings page.

Figure 7B:
FIG. 7B depicts an example display of an MRI image.

FIG. 7B depicts the results of an example MRI building block in a viewport 718 during image review. For instance, the example MRI building block in FIG. 7B may be the MRI building block extending across viewports 704G-H in FIG. 7A. The viewport 718 includes an example of the options icon 710 after it has been selected, which causes the display of the MRI toolbar 720. The MRI toolbar 702 includes a set of options or tools that are applicable to the MRI building block. For instance, the options displayed in the MRI toolbar 720 depend on the type of MRI building block or MRI image. As such, the options displayed in the MRI toolbar 720 may change based on the type of MRI building block or MRI image. In some examples, the order of the options in the MRI toolbar 720 may also change based on the type of MRI building block or MRI image.

The options in the MRI toolbar 720 may include a variety of options for manipulating the MRI image displayed in the viewport 718. For instance, a MIP option may be included. The maximum intensity projection (MIP) option 722 allows for toggling between a two-dimensional (2D) and a MIP view. A views option 724 may also be included in the MRI toolbar 720. The views option 724, when selected, may provide views for the MRI image that may be selected. For example, the displayed "AX" indicates the current view is an axial view. Other potential selectable views from the views option 724 may include sagittal views or coronal views. A subtraction option 726 may also be included in the MRI toolbar 720. The subtraction option 726 allows for MRI subtraction to be toggled on or off. A color option 728 may also be included in the MRI toolbar 720. The color option 728 allows for colorization to be toggled on or off. In some examples, the colorization may also be set to a different threshold (i.e. 50%) through the color option 728. A noise option 730 may also be included in the MRI toolbar 720. The noise option 730 allows for toggling different colorization noise filters for the displayed MRI image. For instance, the colorization noise level may be set to off, low, or high. A lesion highlight option 732 may also be included in the MRI toolbar 720. The lesion highlight option 732 allows for toggling a lesion highlight and focus feature on or off. For instance, the lesion highlight option 732 may be set to off, lesion highlight, or lesion highlight and focus (LH/F). A graph option 734 may also be included in the MRI toolbar 720. The graph option 734 allows for the display of a graph (i.e. contrast enhancement curve) to be turned on and off. A treatment response option 736 may also be included in the MRI toolbar 720. The treatment response option 736 allows for the display of treatment response features to be turned on and off. For each of the options in the MRI toolbar 720, hovering a pointer over any menu option will cause additional information about the particular menu option to provide additional insight to the particular menu option. The foregoing options are illustrative examples, and it should be appreciated that in some examples less than all of the above options may be included in the MRI toolbar 720. In some examples, different or other options may also be included in the MRI toolbar 720.

Figure 7C:
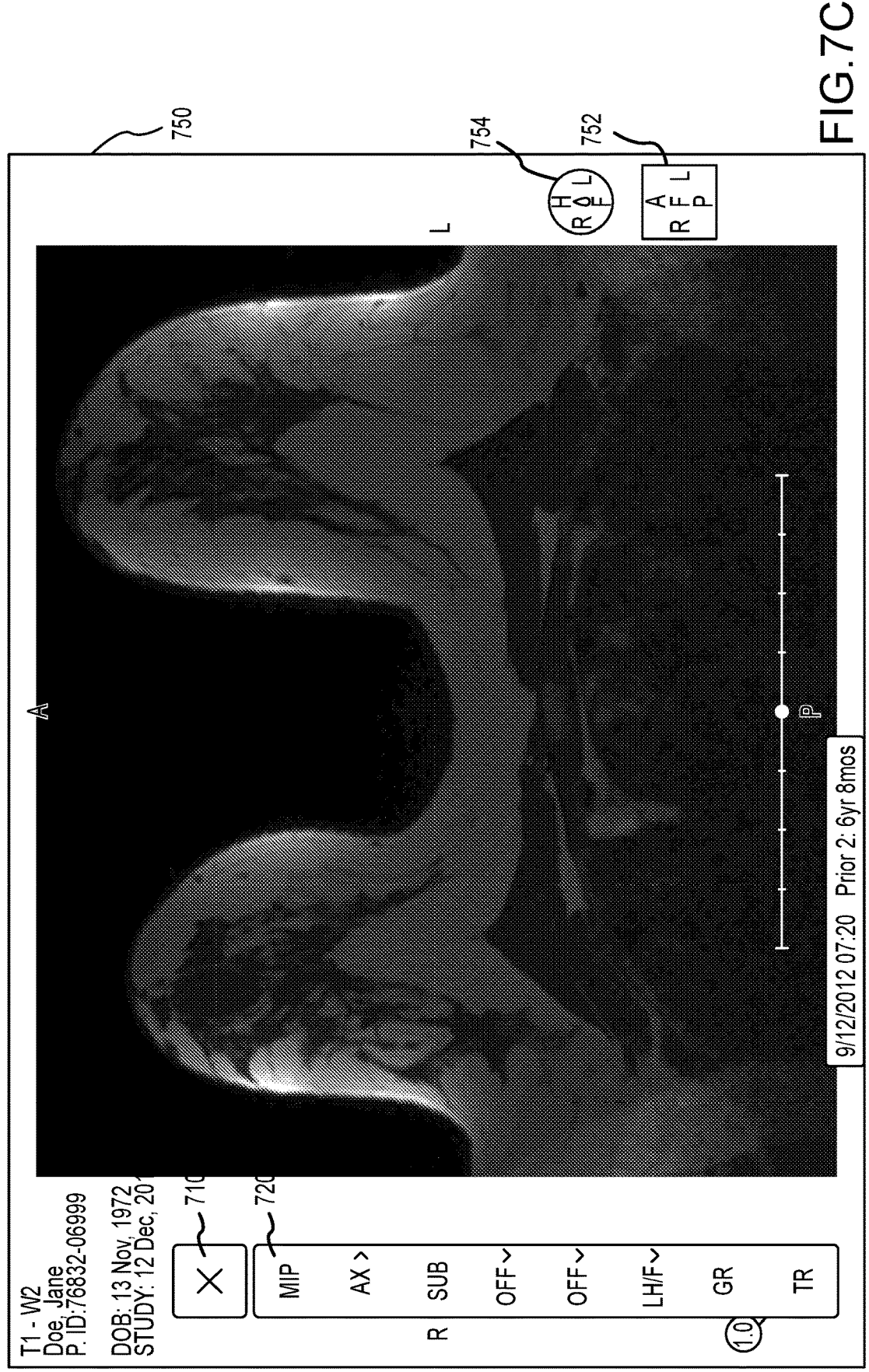
FIG. 7C depicts another example display of an MRI image.

FIG. 7C depicts another example display 750 of an MRI image. The example display 750 also includes the options icon and the MRI toolbar 720. The MRI image also includes an orientation square 752 and an orientation circle 754. The orientation square 752 and the orientation circle 754 indicate the orientation of the patient. For instance, the orientation square 752 includes a set of orientation indicators that correspond to the patient orientation, such as "A" for anterior, "P" for posterior, "R" for right, "L" for left, "H" for head and "F" for foot. The orientation circle 754 includes many similar orientation indicator representations. While the orientation square 752 and the orientation circle 754 provide some indications of orientation, such interface elements can often lead to confusion and may not provide clear guidance regarding the orientation of the MRI image that is being displayed.

Figure 7D:
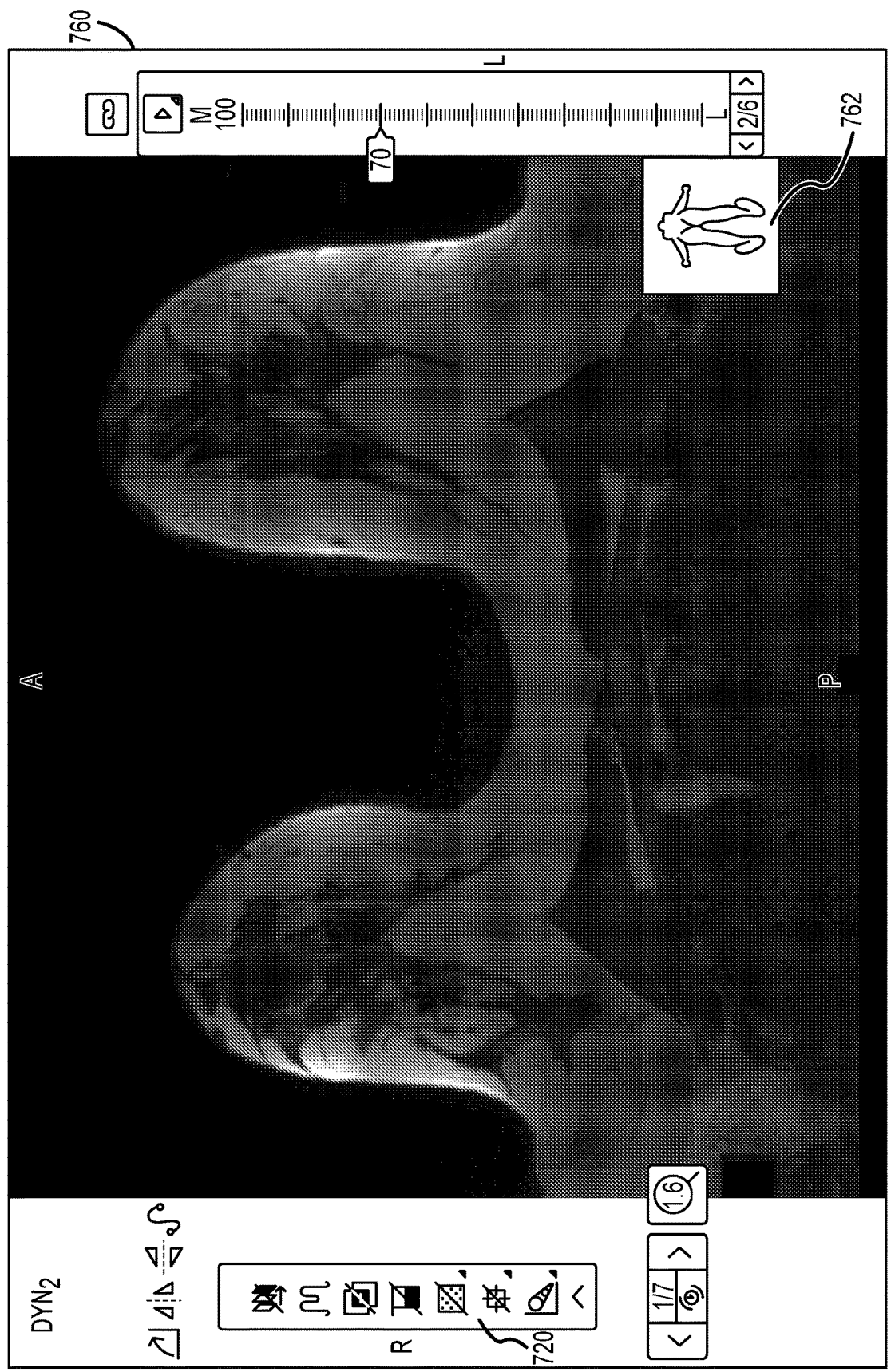
FIG. 7D depicts another example display with a human orientation indicator.
Figure 7E:
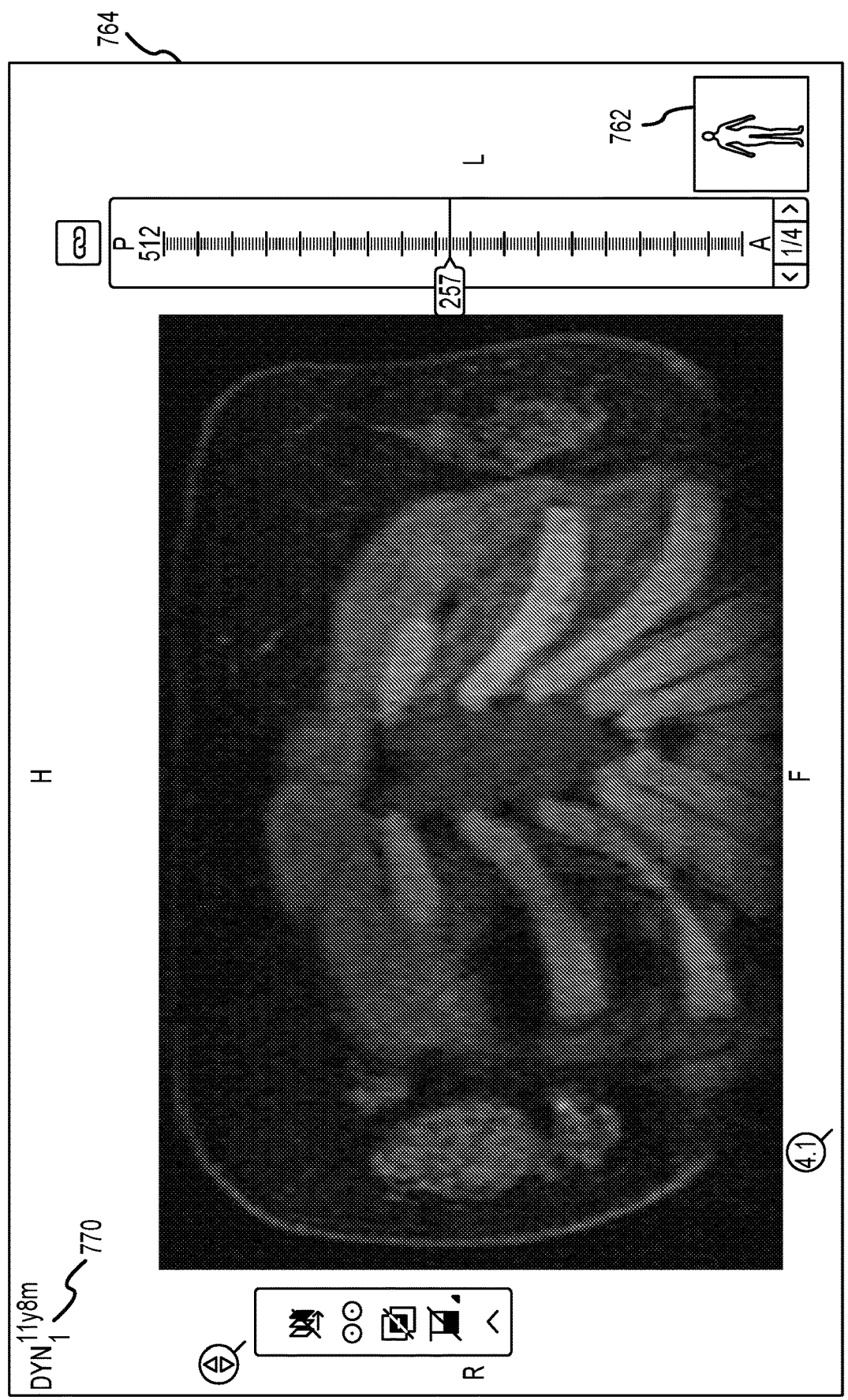
FIG. 7E depicts another example display with a human orientation indicator.

The present technology provides a new guidance system for conveying orientation information of a patient. For example, the present technology may utilize a human figurine in place of the orientation square 752 and/or the orientation circle 754. FIG. 7D depicts an example display 760 with the human orientation indicator 762. The orientation of the patient that corresponds to MRI image is much easier to discern from the human orientation indicator 762. For instance, a quick look at the human orientation indicator 762 reveals that in the MRI image in the example display 760, the view is looking from the patient's feet towards the patient's head, and the right-hand side of the image is the patient's left-hand side. The human orientation indicator 762 may rotate as different images of different orientations are displayed in the display 760. The present technology may determine the orientation for the image by analyzing header information, such as DICOM header information, or analyzing other properties of the displayed image. Once the orientation for the image is determined, the human orientation indicator 762 is displayed in the corresponding orientation. The example display 760 also displays another example of the MRI toolbar 720. FIG. 7E depicts another example display 764 with the human orientation indicator 762 in another orientation. From the orientation of the human orientation indicator 762 in the display 764, a quick determination may be made that the displayed image is of the patient facing the viewer with the head of the patient towards the top of the display 764 and the foot of the patient towards the bottom of the display 764. Changing the orientation of the displayed image will dynamically change the orientation of the human orientation indicator.

The display 764 also includes a compact image reference identifier 770. The image identifier 770 includes the type of image, which is represented by the "DYN". The amount of time that has elapsed since the image was taken is identified by an elapsed time indicator, which is displayed as a superscript to the compact image reference identifier 700 in the example depicted in FIG. 7D. Accordingly, the example image in display 764 was acquired 11 years and 8 months prior to when the image is being displayed. The superscript may also include a color to indicate if the elapsed time is within expected, predetermined, or recommended limits. For example, in breast cancer screening, a screen may be expected or recommended to have occurred annually. Accordingly, if the time elapsed is one year or less, the superscript may appear green. If the time elapsed is between one year and two years, the superscript may appear yellow, and if the time elapsed is greater than two years, the superscript may appear red. Other indicators besides color that connote similar concepts may also be used. In addition, other time frames may also be used. The elapsed time indicator may be in a form other than a subscript number of the compact reference identifier 770. For instance, the elapsed time indicator may be displayed adjacent to the compact reference identifier 770, but not necessarily as a superscript.

A subscript of the compact image reference identifier 770 may indicate a prior image indicator indicating how many images the displayed image is prior to the most recent acquired image. As an example, the prior image indicator may be in the form a subscript number of the compact image reference identifier 770. For example, the "1" subscript for the compact image reference identifier 770 in FIG. 7D indicates that the displayed image was the first prior image acquired prior to the most recent acquired image (the most recent acquired image may have a subscript value of 0). The prior image indicator may also include a color to represent the relative prior number of images. For example, the prior image indicator for prior images 1-3 may appear green. For prior images 4-6, the prior image indicator may appear yellow, and for prior images greater than or equal to 7, the prior image indicator may appear red. Other indicators besides color that connote similar concepts may also be used, and other ranges of prior images may also be used. The prior image indicator may be in a form other than a subscript number of the compact reference identifier 770. For instance, the prior image indicator may be displayed adjacent to the compact reference identifier 770, but not necessarily as a subscript.

Figure 7F:
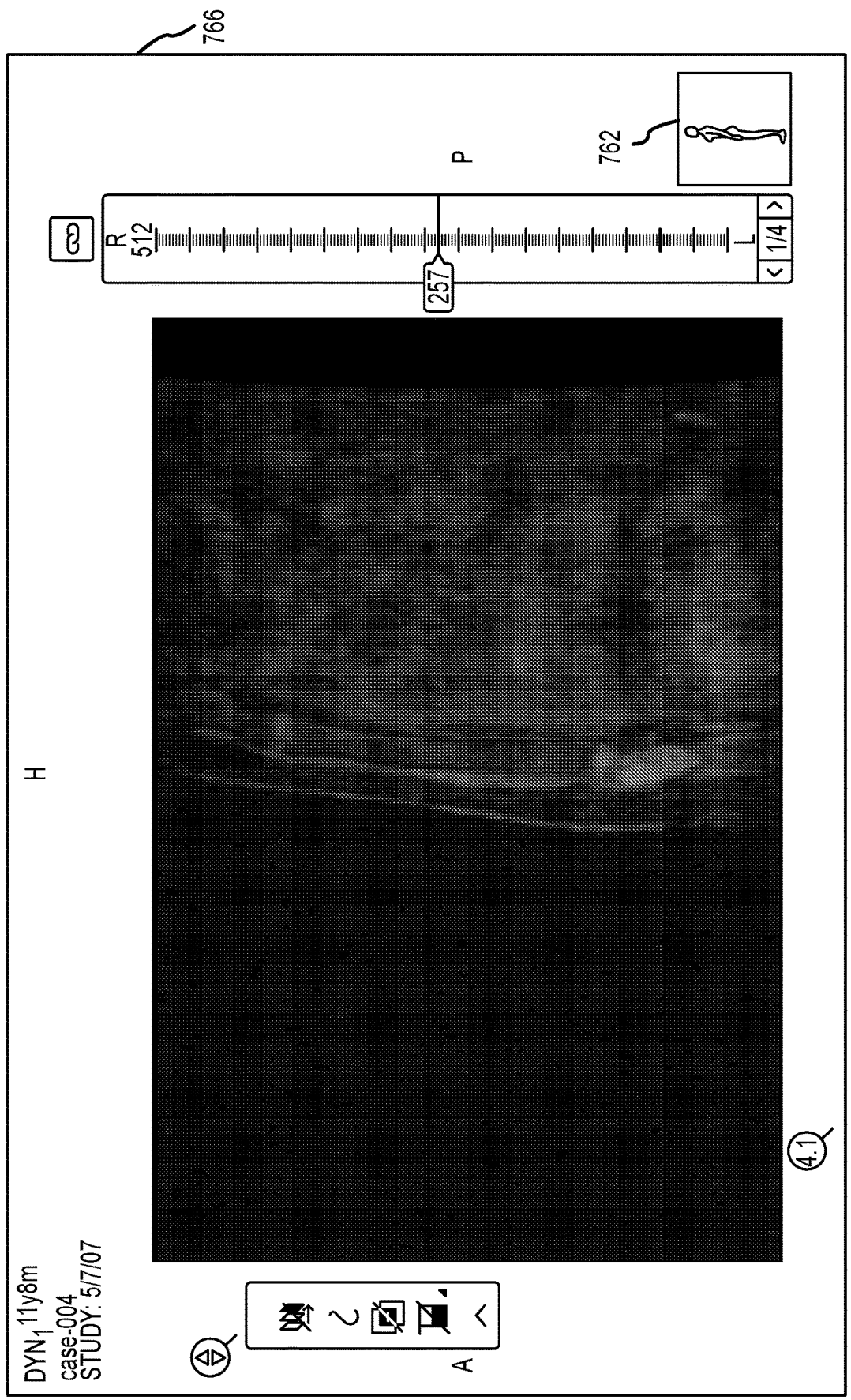
FIG. 7F depicts another example display with a human orientation indicator.

FIG. 7F depicts another example display 766 with the human orientation indicator 762 in yet another orientation. Form the orientation of the human orientation indicator 762 in the display 766, a quick determination may be made that the displayed image is of the patient's left-hand side facing the viewer with the patient's head towards the top of the display 766.

Figure 7G:
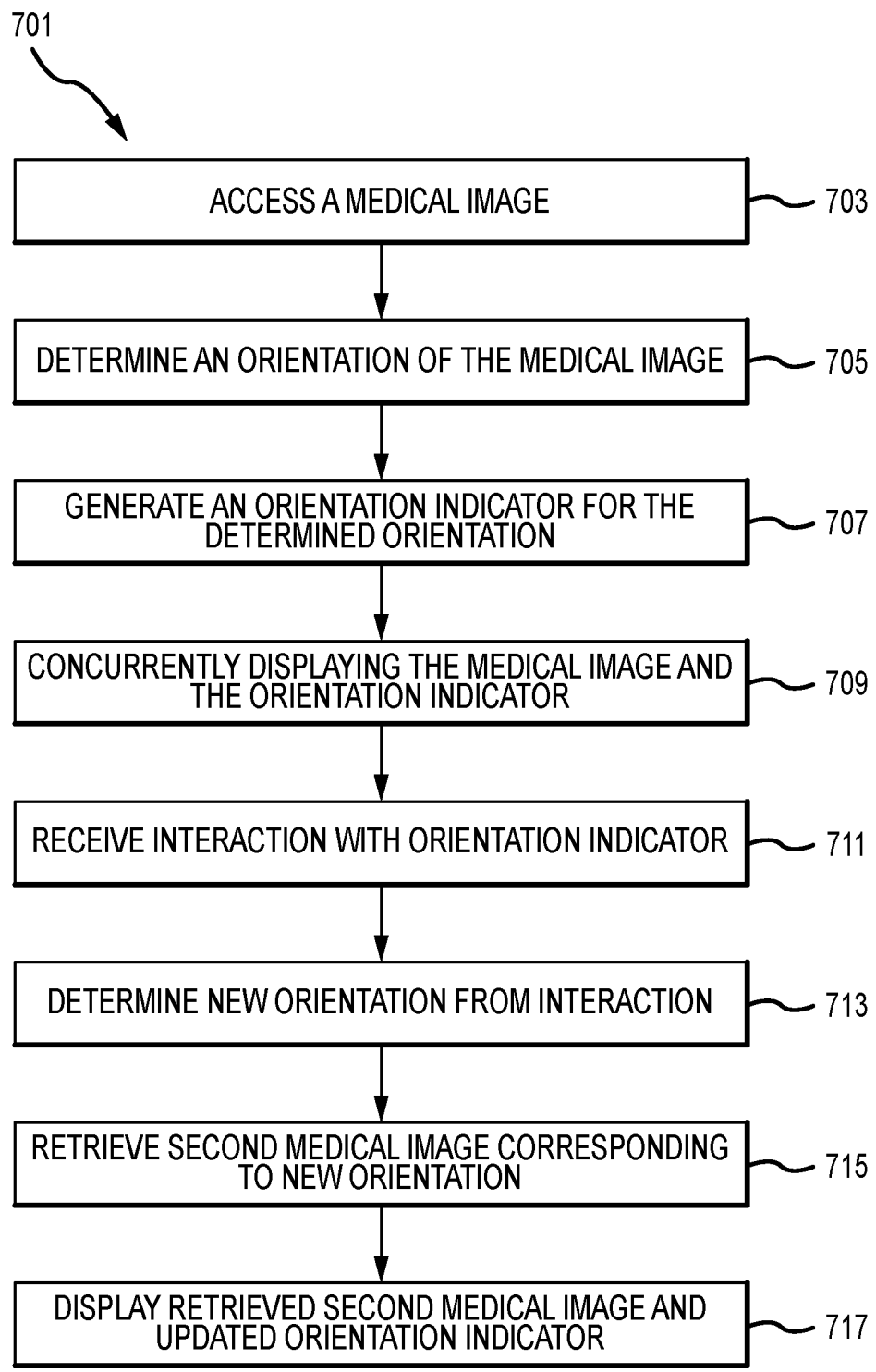
FIG. 7G depicts an example method for displaying orientation data for medical imagery

FIG. 7G depicts an example method 701 for displaying orientation data for medical imagery. At operation 703, a medical image is accessed. The medical image may be an MRI image or an image from another imaging modality. At operation 705, an orientation of the medical image is determined. The orientation of the medical image is the orientation of the patient relative to the imaging modality. The orientation of the medical image may be determined by analyzing data in the header of the medical image or through an analysis of the medical image itself. In some examples, the displayed image orientation may be different than acquired image orientation. In such examples, the displayed image orientation may be used for the orientation determination in operation 705. Once the orientation is determined in operation 705, an orientation indicator is generated for the determined orientation at operation 709. The orientation indicator may be one of the human orientation indicators discussed above. For instance, the orientation indicator may be an image of a human figurine in the determined orientation. The orientation indicator may also be a graphical or schematic depiction of the tissue, anatomy, or portion of the patient that is being imaged. At operation 709, the generated orientation indicator is displayed concurrently with the accessed medical image.

In some examples, the orientation indicator is interactive and may be manipulated to retrieve medical images at different orientations. In such examples, the method 700 may continue to operation 711 where an interaction with the orientation indicator is received. The interaction may include a selection of the orientation indicator with an input device, such as a mouse, pointer, or touch, and a drag or swipe motion to rotate the orientation indicator. In some examples, the interaction may indicate a rotation about the saggital axis, the frontal axis, and/or the vertical axis of the patient. In response to the interaction received at operation 711, a new orientation is determined at operation 713. For example, where the orientation indicator is rotated, the resultant orientation of the orientation indicator is determined to be the new orientation. At operation 715, a second medical image is retrieved that corresponds to the new orientation determined at operation 713. At operation 717, the second medical image is displayed and may be displayed concurrently with the orientation indicator in an updated orientation corresponding to the orientation resulting from the interaction in operation 711.

Figure 8A:
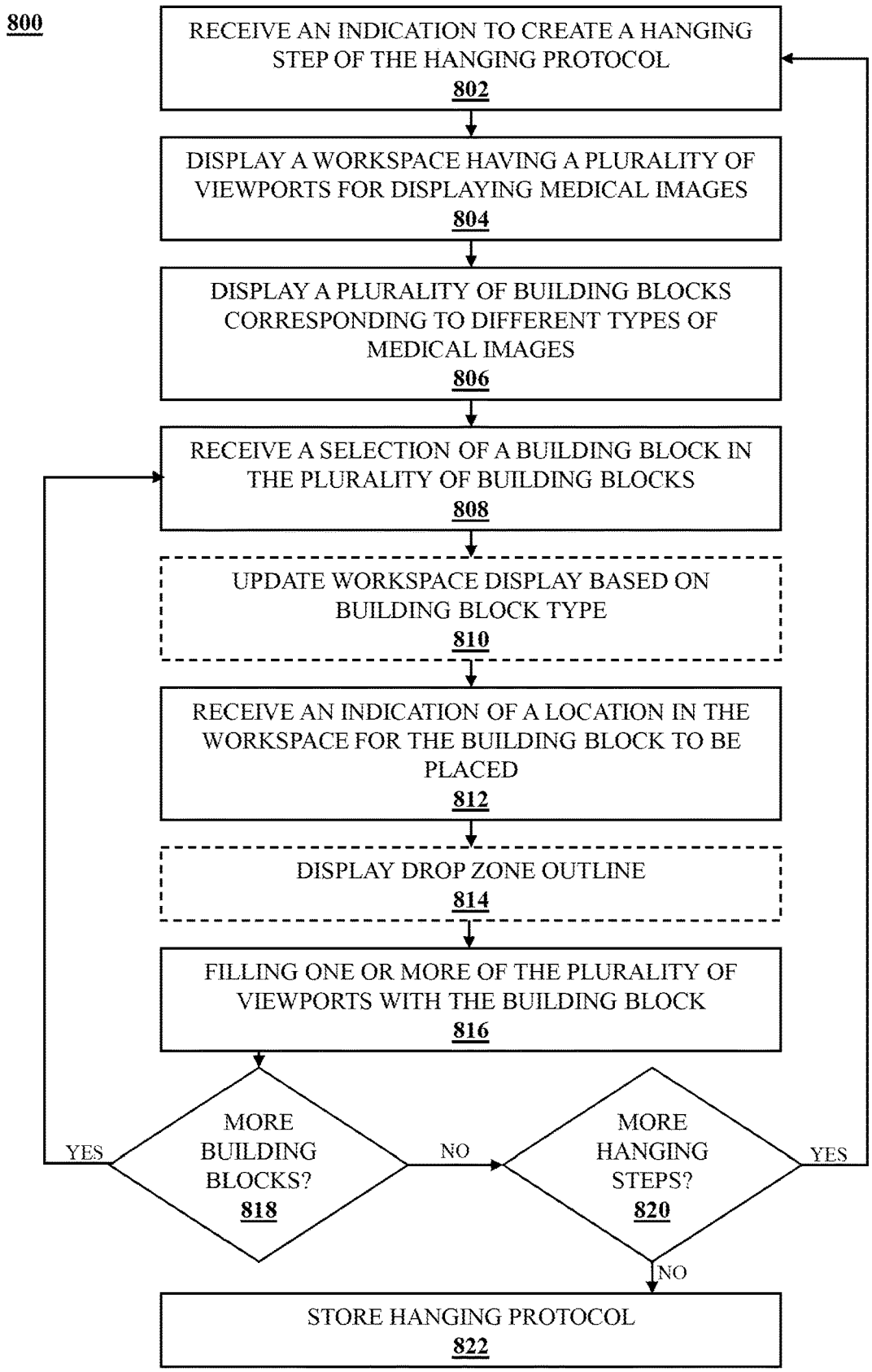
FIG. 8A depicts an example method for generating and using a customized hanging protocol.

FIG. 8A depicts an example method 800 for generating and using a customized hanging protocol. At operation 802 of method 800, an indication is received to create a hanging step of the hanging protocol. The indication may be a user selection to create a new hanging protocol or a new step with the hanging protocol. Where a new hanging protocol is being created, the indicated may be to create a first step of the hanging protocol. Where a hanging protocol is already being developed or customized, the indication may be to create a second or third hanging step. At operation 804, a workspace is displayed that has a plurality of viewports or tiles for displaying medical images. The viewports may be indicated by a smart grid that separates the viewports based on columns and rows. In an example, the workspace may have eight viewports that are displayed in two rows and four columns. The workspace may also include a plurality of hotspots. The hotspots are configured to expand a building block across at least two of the viewports within the workspace. For example, the plurality of hotspots may include at least one of a column hotspot, a row hotspot, a quadruple hotspot, or an octuple hotspot. At operation 806, a plurality of building blocks are displayed. The building blocks correspond to different types or view of medical images. The building blocks may include any of the building blocks discussed above, such as singular or composite building blocks. The building blocks may be displayed in an editor bar that includes a plurality of building block category options. Selection of the building block category options causes the display of additional or different building blocks associated with the category.

At operation 808, a selection of a building block from the plurality of the building blocks is received. The selection may be received via an input device, such as the click of a mouse or through touch input. Once the building block has been selected in operation 808, the display of the workspace may optionally be updated at operation 810 based on the type of building block selected in operation 808. For example, the displayed hotspots may change based on whether the selected building block is a single building block or a composite building block. At operation 812, an indication of a location in the workspace for the building block to be placed is received. The indication of the location may be part of a drag-and-drop interaction where the building block is dragged across the workspace to a desired location. In other examples, the building block may be selected and then the location for the building block may be subsequently selected. At optional operation 814, a drop zone outline for the building block may be displayed based on the location of the building block and, in some examples, the type of the building block and/or the dimensions of the building block. For instance, as the building block is being dragged across the workspace, the drop zone outline is displayed based on the current location of the building block as it is being dragged across the workspace. In an example, while the selected building block is dragged across the workspace, the drop zone outline is displayed and dynamically updated based on a location of the building block relative to the workspace as it is being dragged. The drop zone outline dynamically highlights one or more of the plurality of viewports for which the first building block will fill if it were dropped at the present location during the drag operation. For example, if the building block is dragged over a hotspot, the number of viewports that are highlighted by the drop zone outline corresponds to the type of hotspot. At operation 816, one or more of the plurality of viewports is filled with the selected building block based on the indicated location in the workspace received in operation 812. The number of viewports that are filled depends on whether the indicated location is a hotspot and the type or dimensions of the selected building block.

At operation 818, a determination may be made as to whether more building blocks are to be added to the workspace of the current hanging step. If more building blocks are to be added, the method 800 flows back to operation 808 where operations 808-818 are repeated for a second building block. For example, once a first viewport is filled with a first building block, another viewport may be filled with a second building block. This process may continue until all the viewports of the workspace for the current hanging step are filled. In some examples, the different building blocks used to fill the workspace may correspond to different imaging modalities. For instance, a first building block may correspond to a first imaging modality, such as an x-ray imaging modality, and the second building block may correspond to a second imaging modality, such as an MRI imaging modality. If there are no additional building blocks that are to be added to the workspace of the current hanging step, the process flows from operation 818 to operation 820 where a determination is made as to whether more hanging steps are to be added to the hanging protocol. If more hanging steps are to be added, the method 800 flows back to operation 802 where operations 802-820 are repeated for another hanging step in the hanging protocol. For instance, a second hanging step may be generated where a second workspace corresponding to the second hanging step is populated with a plurality of building blocks. If no additional hanging steps are to be added to the hanging protocol, the process flows from operation 820 to operation 822 where the hanging protocol as customized by method 800 is stored for later importation of medical images of a patient according to the filled viewports of the workspace. The customized hanging protocol may be stored locally or remotely such that it can be accessed from different devices or workstations. The hanging protocol may also be stored such that others have limited access to access or edit the hanging protocol.

Figure 8B:
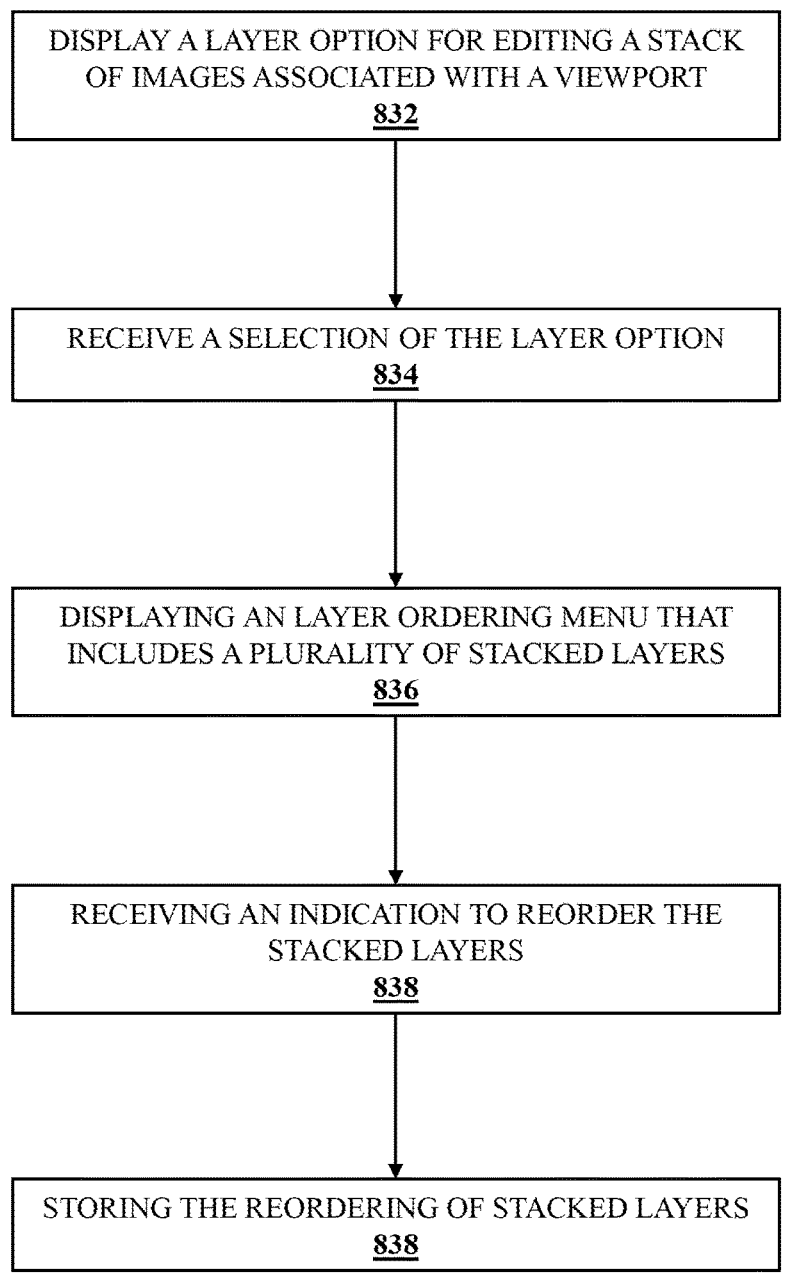
FIG. 8B depicts an example method for configuring a stack of images or views in a viewport of a hanging protocol.

FIG. 8B depicts an example method 830 for configuring a stack of images or views in a viewport of a hanging protocol. The method 830 may be performed as part of, or in conjunction with, the method 800 depicted in FIG. 8A. At operation 832 of method 830, a layer option is displayed within a viewport that has been filled with a building block. The layer option is provided for editing layers of images or views associated with the filled viewport. At operation 834, a selection of the layer option is received, and upon receiving the selection of the layer option, a layer ordering menu is displayed at operation 836. The layer ordering menu includes a plurality of stacked layers corresponding to medical images. At operation 838, an indication is received to add, remove, or reorder one or more of the layers in the stacked layers. The indication to add one or more layers may be received via a selection of an add layer option and the indication to remove one or more layers may be received via a selection of a delete layer option. The indication to reorder the layers may be received via a drag and drop reordering of the displayed layers in the layer ordering menu. The indication to reorder the layers may also be made through the selection of up and down arrows (or similar indicators) displayed within each of the displayed layers in the layer ordering menu. At operation 838, the reordering of the stacked layers may be stored. Storing the reordering of the stacked layers may be triggering by the selection of a confirmatory option, such as an apply button, displayed within the layer ordering menu.

Figure 8C:
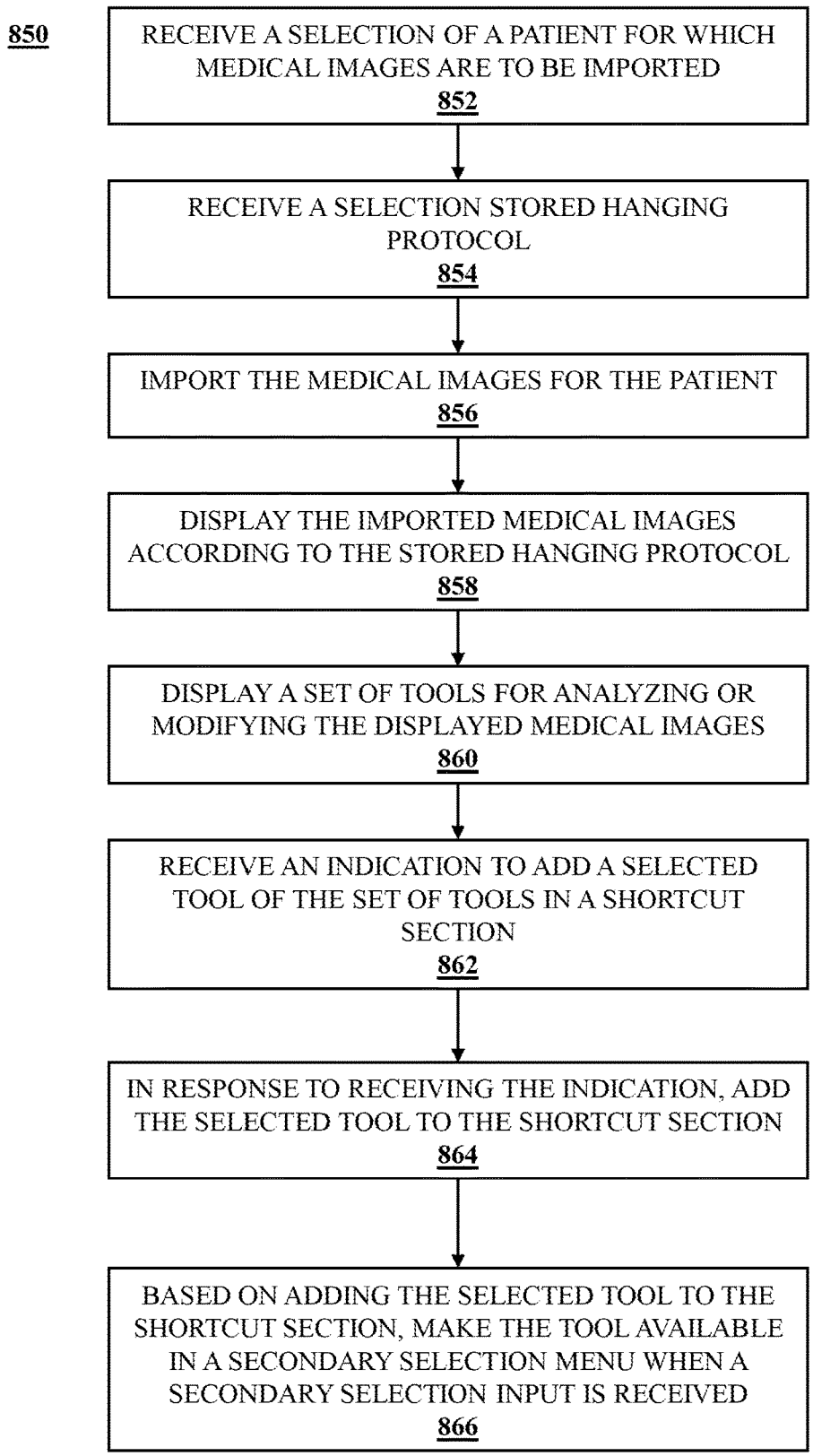
FIG. 8C depicts an example method for displaying medical images of a patient according to a stored hanging protocol.

FIG. 8C depicts an example method 850 for displaying medical images of a patient according to a stored hanging protocol. At operation 852, a selection of a patient for which medical images are to be imported is received. The selection may be received from a user selecting the patient's name from a list of patient names for which medical images are available. At operation 854, a selection of a stored hanging protocol is received. The selection may be received from a user, such as a radiologist, selected a hanging protocol that the radiologist previously customized and stored. The selected hanging protocol may also be a hanging protocol that was customized by another radiologist and shared, or otherwise made accessible, to the current user or radiologist. In some examples, the selection of the stored hanging protocol may be made automatically according to a default hanging protocol that is associated with the current user or radiologist. The stored hanging protocol may also be modified by stored personal preferences of the user or radiologist performing the review. For example, where certain options of a building block or viewport of the hanging protocol have been set to a value of "user preference" (or equivalent setting), the stored user settings for the present user selecting the hanging protocol in operation 854 may be accessed or retrieved. Those accessed user preferences may then be used to modify the selected hanging protocol according to the options set within the hanging protocol. At operation 856, medical images for the selected patient are imported. The medical images may be present locally on the device executing the method 850 or may be retrieved from a remote source, such as one or more other workstations within a cluster or from a PACS. At operation 858, the imported medical images are displayed according the selected stored hanging protocol.

At operation 860, a set of tools for analyzing or modifying the displayed medical images is displayed. The set of tools may be displayed in a chrome displayed adjacent to the medical images. The set of tools may also be displayed upon the selection of a tools icon, which also may be displayed within the chrome. The set of tools may include at least one of a magnification, continuous zoom, ellipse, ruler, reset, or close study tool. At operation 862, an indication to add a selected tool of the set of tools into a shortcut section is received. In some examples, the shortcut section may be displayed in the chrome. In other examples, the shortcut section may be moved or relocated to other areas of the workspace. The indication to add the selected tool to the shortcut section may be received as a drag-and-drop operation. For instance, a user may drag the tool from the set of tools into the shortcut section. In response to receiving the indication to add the tool to the shortcut section, the selected tool is added to the shortcut section in operation 864. In operation 866, based on adding the selected tool to the shortcut section, the selecting tool is made available, or added to, a secondary selection menu that is accessible from a secondary selection, such as a right-click of a mouse or long press on a touch screen. As such, when a user makes a secondary selection anywhere over the displayed medical images, the secondary selection menu with the customized tools is displayed at the location of the secondary selection. Such a feature provides a benefit to the analysis of the radiologist. When a radiologist identifies a potential abnormality in a medical image, the radiologist does not want to navigate away from the identified abnormality to continue the analysis. By having the desired tools for additional markup or analysis readily available at any location where an abnormality may be identified provides a useful improvement to the user interface for the radiologist.

In populating the viewports of the hanging protocols, the medical image corresponding to the building block is retrieved and displayed. Images from some imaging modalities are easier to identify and retrieve than others. For example, mammography offers well defined and standardized view labels with associated modifiers, which uniquely identify and represent each acquired image/view, thus allowing the creation of well-defined hanging protocols for image review on a diagnostic workstation. Unlike mammography, MRI does not offer similar standardized labeling to associate the different types of images or volumes acquired during a breast MRI examination.

Some additional details regarding MRI images is useful to understand the complexity of MRI image data. In MRI imaging, three dimensional (i.e., volumetric) imaging information of a region of a patient's body is acquired and displayed for diagnostic purposes. The MRI information may be acquired using a variety of modalities or protocols and a number of different acquisition devices.

When a substance such as human tissue is subjected to a uniform magnetic field (polarizing field $B_0$), the individual magnetic moments of the excited nuclei in the tissue attempt to align with this polarizing field, but process about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment Mt. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

The measurement cycle used to acquire each MR signal is performed under the direction of a pulse sequence produced by a pulse sequencer. Clinically available MRI systems, for example, store a library of such pulse sequences that can be prescribed to meet the needs of many different clinical applications.

After image reconstruction, the reconstructed image is stored in an MRI image file, which can be stored either locally, or in a Picture Archive Communication System (PACS). MR image files are usually in a vendor-independent format called Digital Imaging and Communications in Medicine ("DICOM"). Using the DICOM format, each MR image file has a header portion and a body portion. The header portion contains information similar to that located in the raw data header as well as information about the specific corresponding imaging slice, e.g. image slice number. The body portion contains the actual image data. Typically, each MR image file contains image data about one imaging slice.

There are a number of parameters that influence the strength of the signal obtained from an MRI scanner, and the appearance of the acquired image. Some of these parameters are controlled by the operator of the scanner, such as the repetition time ("TR"), the echo time ("TE"), and the flip angle α. Other parameters are characteristics of the tissue being studied, such as the relaxation times $T_1$ and $T_2$. In principle, the unambiguous interpretation of an image involves only the observation and determination of the tissue dependent parameters, such as $T_1$ and $T_2$. In practice, however, these parameters are at least partially obscured by differing selections of TR and TE.

Image contrast between tissue components results from differential rates of "relaxation", i.e., the transition from transverse magnetization back to longitudinal magnetization. $T_1$ and $T_2$ are two different relaxation constants that result in different image contrast highlighting different tissue components. To create a $T_1$-weighted image, magnetization of the tissue is allowed to recover before measuring the MR signal by changing the TR. This image weighting is useful for post-contrast imaging. To create a $T_2$-weighted image, magnetization of the tissue is allowed to decay before measuring the MR signal by changing the TE. The MRI image can be biased toward either $T_1$-weighted or $T_2$-weighted images, and thereby vary the contrast between tissue components (e.g., fat, muscle, and water), by choosing imaging parameters for the MRI scan, resulting in different image acquisition protocols. In $T_1$-weighted MRI images, fat has higher contrast and water has lower contrast. In $T_2$-weighted MRI images, water has lower contrast and fat has higher contrast. In both $T_1$ and $T_2$ weighted MRI images, air and dense bone (no fat) has the lowest contrast.

Commercially available computer-controlled workstations employ a number of common types of displays to communicate MRI information to a reviewer. For example, MRI displays for the study of breast tissue, e.g., to identify the presence and location of cancer lesions, are well-known. Such MRI displays for breast tissue typically display images showing various two-dimensional slices taken through one or both breasts, and provide the reviewer with the ability to scroll through the respective tissue image slices using a common device, such as mouse. This scrolling enables the reviewer to readily view different slices, eventually covering the entire breast region.

A system operator (e.g., a radiologist, technician, or other medical professional) may employ the MRI scanner to acquire volumetric image information of the patient tissue (e.g., a breast) using different MRI parameters to emphasize different physiological information. For example, $T_2$-weighted images may be acquired with one set of acquisition parameters, and would show different information from $T_1$-weighted images acquired with different scanner parameters. In addition, a set of images (e.g., $T_1$-weighted) may be acquired before the administration of a contrast agent, and thereafter for several time periods after the contrast agent has entered the blood stream.

Typical MRI image acquisition protocols include $T_2$-weighted and multi-phase $T_1$-weighted series/sequences. Some MRI image acquisition protocols also include high-resolution $T_1$-weighted sequences for anatomy clinical readout only. Multi-phase $T_1$-weighted sequences can include pre-contrast and post-contrast $T_1$-w sequences and dynamic series. Other MRI image acquisition protocols also include advanced diffusion sequences, which measure the diffusion of water molecules in biological tissues.

As discussed above, current HPs vary between acquisition system manufacturers and between acquisition systems. HPs also vary depending on specific MRI parameters as set forth by a system operator for each acquisition system. Accordingly, one way to improve reading efficiency and throughput is to implement a universal HP that is not dependent on manufacturer, acquisition system or operator-set parameters, but rather sorts the MRI data based on relevant physiological parameters/data of interest to the reviewer.

Different functional series/sequences in MRI data can be differentiated by analyzing acquisition settings in the MRI data's DICOM header. For instance, a limited number of consistent functional sequences are used in breast MRI image acquisition protocols. These include $T_1$-weighted and $T_2$-weighted sequences.

$T_1$-weighted and $T_2$-weighted images/sequences can be differentiated using TR and TE. $T_1$-weighted images/sequences typically have a short TR and a short TE. $T_2$-weighted images/sequences typically have a long TR and a long TE. Proton density-weighted ("Rho-weighed") sequences typically have a long TR and a short TE. For clinical MRI, TE is typically shorter than TR. A short TR is typically less than 500 ms (the approximate average TR for a $T_1$-weighted image/sequence). A long is typically greater than 1,500 ms. A short TE is typically less than 30 ms. A long TE is typically greater than 90 ms.

Most breast MRI image acquisition protocols include only $T_1$-weighted and $T_2$-weighted (with or without fat saturation) sequences to reduce procedure time. However, MRI image acquisition protocols can also include the following classes of sequences: dynamic sequences; pre-contrast dynamic $T_1$-weighted; first post-contrast dynamic $T_1$-weighted; delay post-contrast dynamic $T_1$-weighted; pre or post high resolution $T_1$-weighted (with or without fat saturation); diffusion weighted imaging ("DWI"); and derived series images with motion correction ("MOCO").

U.S. Patent Publication No. 2015/0260816, assigned to Hologic, Inc., which is incorporated by reference in its entirety, describes methods for categorizing MRI images. For instance. A computer may receive the MRI data in the DICOM format, including the DICOM header. The computer may then extract the protocol details from the DICOM header. Protocol details may include at least: TR; TE; fractional anisotropy ("FA"); inversion time ("TI"); strength of magnetic gradient ("b-value"); sequence type; and derived/secondary.

If derived/secondary details are identified in the DICOM header, the MRI data is categorized as a derived series with MOCO. If b-values are identified in the DICOM header, the MRI data is categorized as DWI. Diffusion sequences (DWI) can be identified by identifying b-values in their DICOM headings. Diffusion sequences can also be identified by their distinctive echo planar (EPI) sequences. If TR from the DICOM header is less than 500 ms and TE from the DICOM header is less than 30 ms, the MRI data is categorized as a $T_1$-weighted sequence. On the other hand, if TR from the DICOM header is greater than 1,200 ms and TE from the DICOM header is greater than 90 ms, the MRI data is categorized as a $T_2$-weighted sequence.

For MRI data that has been categorized as a $T_1$-weighted sequence, the DICOM header may be further analyzed. In analyzing the DICOM header, if the spatial resolution from the DICOM header is high, the MRI data is categorized as a high resolution $T_1$-weighted sequence. If the spatial resolution from the DICOM header is low, the MRI data is categorized as a low resolution $T_1$-weighted sequence. While high and low spatial resolution are relative terms, in some embodiments, high spatial resolution can be any resolution smaller than 0.8-1.0 mm and low spatial resolution can be any resolution larger than 0.8-1.0 mm.

In high resolution $T_1$-weighted sequences, if the DICOM header includes an inversion time, the sequence is additionally categorized as having fat saturation. If the DICOM header does not include an inversion time, the sequence is additionally categorized as not having fat saturation.

In low resolution $T_1$-weighted sequences, if the DICOM header does not include identical TR and TE with a delay of less than 0.5 ms, the MRI data is categorized as an individual low resolution $T_1$-weighted sequence. If the DICOM header does include identical TR and TE with a delay of less than 0.5 ms, the MRI data is categorized as a potential dynamic sequence.

In individual low resolution $T_1$-weighted sequences, if the DICOM header includes an inversion time, the sequence is additionally categorized as having fat saturation. If the DICOM header does not include an inversion time, the sequence is additionally categorized as not having fat saturation.

For MRI data categorized as a potential dynamic sequence, if the DICOM header includes identical fractional anisotropy values, the MRI data is categorized as a raw dynamic sequence. If the DICOM header does not include identical fractional anisotropy values, the MRI data is categorized as a potential $T_1$ mapping sequence.

For MRI data categorized as a raw dynamic sequence, if the DICOM header includes slice numbers and left and right orientation values, then MRI data is further categorized as a dynamic sequence. Further, timing information in the DICOM header can be used to further categorize the MRI data as pre-contrast, first post-contrast, and delay post-contrast dynamic $T_1$-weighted sequences, with first and delay subtractions. As described above, dynamic sequences can also be distinguished from high resolution $T_1$-weighted sequences by comparing imaging spatial resolutions.

For MRI data categorized as a potential T1 mapping sequence, if the DICOM header includes a plurality of flip angles, with other acquisition parameters associate with each flip angle being identical, the MRI data is categorized as a T1 mapping sequence. The various flip angle T1 mapping sequences can include dynamic pre data. In such cases, the various T1 mapping acquisition sequences can repeat dynamic pre data with the only changed parameter being the flip angle.

For MRI data that has been categorized as a $T_2$-weighted sequence, if the DICOM header includes an inversion time, the sequence is additionally categorized as having fat saturation. If the DICOM header does not include an inversion time, the sequence is additionally categorized as not having fat saturation.

Categorization of the MRI data and image sequences may only be beneficial to the extent such categorization ca be utilized. The present technology allows for the generation of at least two standardized labels that may be used to tag MRI images. FIG. 9A depicts a sample first tag or label as well as a table 902 that defines the sample first tag. The first tag or label offers multiple levels of information within a single multi-digit label. Each digit of the label represents a different feature, property, and or characteristic of the MRI data that has been analyzed. For instance, the first digit may represent a first level of information, such basic functions of the MRI data (e.g., contrast enhancing dynamic sequence). The second digit represents a second level of information, such as the type of fat separation technique that was used during acquisition of the MRI data. The third digit represents a third level of information, such as subtypes of functional groups (e.g., low vs. high spatial resolution). The fourth digit represents a third level of information, such as whether motion correction was performed. The fifth digit may represent a fifth level of information, such as version information for the MRI data.

The table 902 provides an example of how a five-digit label may be defined. For example, if the MRI data is a $T_1$-weighted sequence, the first digit of the label is a 1. If the MRI data is a $T_2$-weighted sequence, the first digit of the label is a 2. If the MRI data is a dynamic sequence, the first digit of the label is a 3. If the MRI data is a diffusion weighted sequence, the first digit of the label is a 4. If the MRI data is a susceptibility weighted sequence, the first digit of the label is a 5. If the MRI data cannot be categorized in one of the foregoing categories, the first digit of the label may be a 6, representing miscellaneous or uncategorized data.

At the second level, the fat separation of the MRI data is represented. For example, if the MRI data is non fat saturated (non FAT SAT), the second digit of the label is a 1. If the MRI data is fat saturated (FAT SAT), the second digit of the label is a 2.

At the third level, additional subtypes of functional groups are represented. For example, for a $T_1$-weighted sequence or a $T_2$-weighted sequence with low spatial resolution, the third digit of the label is a 1. For a $T_1$-weighted sequence or a $T_2$-weighted sequence with high spatial resolution, the third digit of the label is a 2. For a dynamic sequence having a low temporal resolution, the third digit of the label is a 1. For a dynamic sequence having a high temporal resolution, the third digit of label is a 2. For a dynamic sequence that is abbreviated (such as having only two dynamic phases), the third digit of the label is a 3. For a diffusion weighted sequence is a diffusion subtype, the third digit of the label is a 1 and if the subtype is a diffusion tensor, the third digit of the label is a 2.

At the fourth level, qualifiers such as motion correction may be represented. For example, if motion correction (MOCO) has been applied, the fourth digit of the label is a 1. If no motion correction has been applied, the fourth digit may be a zero or omitted. At the fifth level, the version of the motion correction may be represented by the actual version number. For instance, if the version of motion correction is the first version, the fifth digit in the tag is a 1.

The example tag in FIG. 9A (i.e., 32112) thus represents a dynamic sequence that is FAT SAT with a low temporal resolution that has had a second version of motion correction applied. While the specific example above uses numbers and five digits for the label, it should be appreciated that letters or other indicia may also be utilized for the label to represent similar information, and the number of digits may be greater or fewer than five. In addition, the digits may appear in different orders and in some examples, represent additional or different information regarding the MRI data. Once the label is generated, the label may be stored in the head of the analyzed MRI data or otherwise stored as associated with the MRI data. For instance, the label may be stored as metadata of the MRI data.

FIG. 9B depicts an example second tag or label as well as a table 902 that defines the sample second tag. Like the example first tag discussed above, the first tag or label offers multiple levels of information within a single multi-digit label. Each digit of the label represents a different feature, property, and or characteristic of the MRI data that has been analyzed. In the example depicted, the second label represents additional information about post-processing maps that have been generated on top of the original MRI data.

For the second tag, the first digit represents a mapping type. For example, if the mapping is a diffusion mapping, the first digit of the label is a 1. If the mapping is a DCE mapping, the first digit of the label is a 2. Additional mapping labels may be represented by the second digit of the label. For diffusion mappings, if the mapping is an apparent diffusion coefficient (ADC) mapping, the second digit is a 1. If the mapping is a direction mapping, the second digit is a two, and if the mapping is a vector mapping, the second digit is a 3.

For DCE mappings, if the mapping is a standard or semi-quantitative DCE map, the second digit of the label is a 1. If the mapping is a $K_{trans}$ mapping, the second digit of the label is a 2. If the mapping is $K_{ep}$ mapping, the second digit of the label is a 3, and if the mapping is an initial area under the time-to-signal intensity curve (IAUC) mapping, the second digit of the label is a 4.

The third digit of the second label represents mapping version information. For example, the mapping is pixel value based version, then the third digit of the label is a 1. If the mapping is a concentration version, the third digit of the label is a 2. Accordingly, the sample second tag in FIG. 9B (i.e., 222), represents a concentration estimation based $K_{trans}$ DCE mapping.

Figure 10:
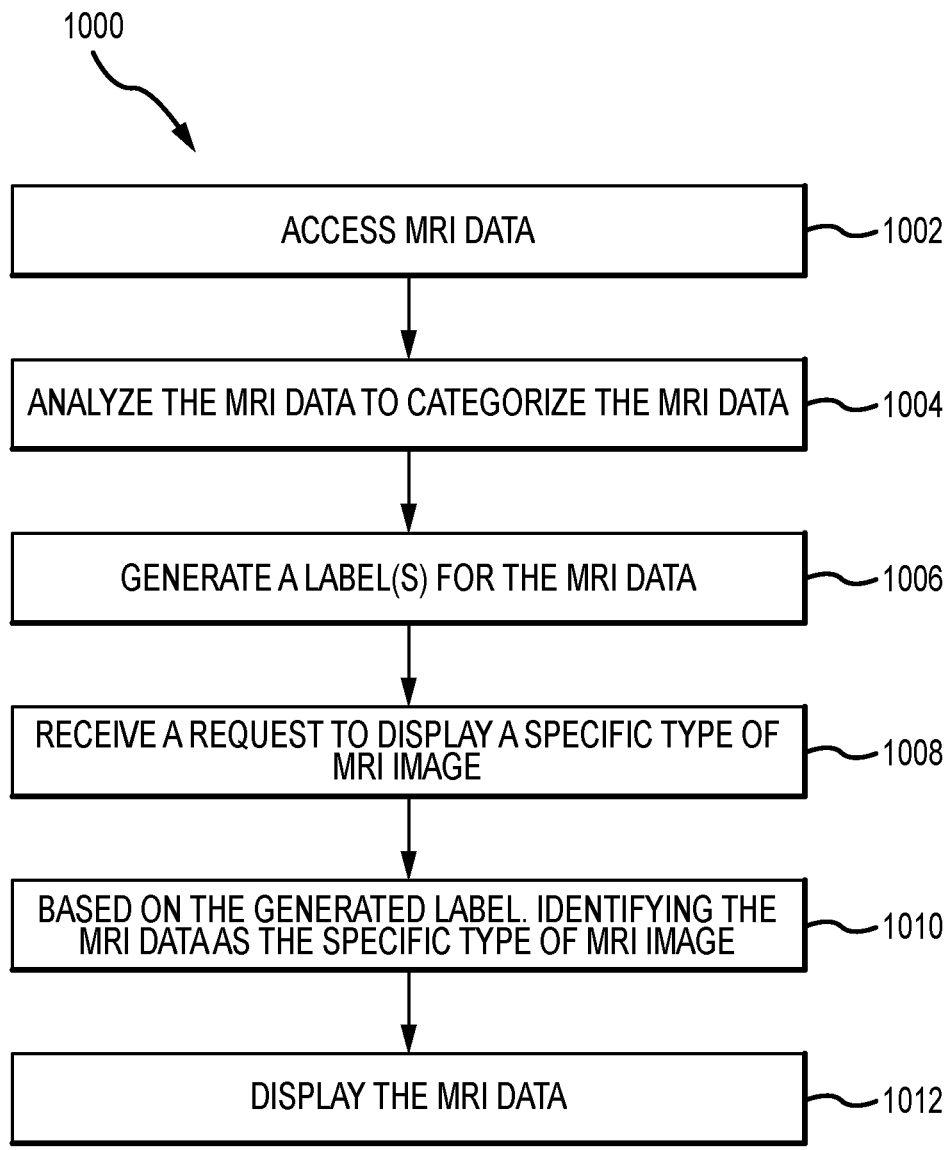
FIG. 10 represents an example method for populating a viewport of a hanging protocol.

FIG. 10 represents an example method 1000 for populating a viewport of a hanging protocol with the above categorizations and tags. At operation 1002, MRI data is accessed by a computer or processing device. At operation 1004, the MRI data is analyzed to categorize the MRI data. Categorizing and analyzing the MRI data may be accomplished by performing the processes discussed above. At operation 1006, at least one label or tag is generated for the MRI data based on the categorization for the MRI data in operation 1004. As an example, operation 1006 may include generating a first label, such as the example first label discussed above with reference to FIG. 9A. Operation 1006 may also include generating a second label, such as the example second label discussed above with reference to FIG. 9B. The generated labels may be stored in the MRI data, such as a header or other associated metadata.

At operation 1008, a request to display a specific type of MRI image is received. The request may be associated with a viewport of a hanging protocol. For example, a building block for a specific type of MRI data may be in a hanging protocol. When the hanging protocol is processed, a request for images corresponding to the building blocks may be generated. At operation 1010, based on the generated label(s) in operation 1006, the MRI data is identified as the specific type of MRI image that was requested in operation 1008. For example, properties of the specific type of MRI image may be translated or converted to a format that is the same as the label(s). That converted information may be used to query a dataset including the MRI data. The query results in MRI data having a matching label. The specific type of MRI image requested may also be compared against the generated label(s) to identify the MRI data as the specific type of MRI image that has been requested. The MRI data may then be displayed in operation 1012 in response to the request received in operation 1008.

As should be appreciated, while the above methods have been described in particular orders, no such order is inherently necessary for each operation identified in the methods. For instance, the operations identified in the methods may be performed concurrently with other operations or in different orders. In addition, the methods described above may be performed by the systems described herein. For example, a system may have at least one processor and memory storing instructions that, when executed by the at least one processor, cause the system to perform the methods described herein.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C.

Although specific embodiments are described herein, the scope of the technology is not limited to those specific embodiments. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A computer-implemented method for generating a customized hanging protocol for the display of medical images, the method comprising:
   receiving an indication to create a first part of the hanging protocol;
   displaying a workspace having a plurality of viewports for displaying medical images;
   displaying a plurality of building blocks corresponding to different types of medical images;
   receiving a selection of a first building block in the plurality of building blocks, wherein the first building block corresponds to a first type of medical image;
   receiving an indication of a location in the workspace for the first building block to be placed;
   based on the indication of the location in the workspace for the first building block, filling one or more of the plurality of viewports with the first building block, a number of the filled one or more plurality of viewports being based on whether the first building block is a single building block or a combination of building blocks;
   receiving a selection of a second building block in the plurality of building blocks, wherein the second building block corresponds to a second type of medical image;
   receiving an indication of a location in the workspace for the second building block to be placed;
   based on the indication of the location in the workspace for the second building block, filling another one or more of the plurality of viewports with the second building block, a number of the filled another one or more of the plurality of viewports being based on whether the second building block is a single building block or a combination of building blocks; and
   storing the first part of the hanging protocol for importation of medical images of a patient according to the filled viewports in the workspace.

2. The computer-implemented method of claim 1, wherein the first building block corresponds to a first imaging modality and the second building block corresponds to a second imaging modality.

3. The computer-implemented method of claim 1, wherein the workspace includes a plurality of hotspots, each of the hotspots configured to expand a building block across at least two viewports.

4. The computer-implemented method of claim 3, wherein the plurality of hotspots include at least one of a column hotspot, a row hotspot, a quadruple hotspot, or an octuple hotspot.

5. The computer-implemented method of claim 1, wherein the indication of a location in the workspace for the first building block is received via a drag and drop interaction.

6. The computer-implemented method of claim 1, further comprising displaying a drop zone outline based on whether the first or second building block is a single building block or any combination of building blocks.

7. The computer-implemented method of claim 1, wherein the first building block is a composite building block.

8. The computer-implemented method of claim 1, wherein the plurality of building blocks are displayed in an editor bar with a plurality of building block category options.

9. The computer-implemented method of claim 1, further comprising, based on whether the first building block is a single building block or any combination of building blocks, updating a layout of the workspace upon selection the first building block.

10. The computer-implemented method of claim 1, further comprising:
receiving an indication to create a second part of the hanging protocol;
displaying a second workspace having a plurality of viewports for displaying medical images;
displaying a plurality of building blocks corresponding to different types of medical images;
receiving a selection of a third building block in the plurality of building blocks;
receiving an indication of a location in the second workspace for the third building block to be placed;
based on the indication of the location in the second workspace for the third building block, filling one or more of the plurality of viewports with the first building block; and
storing the second part of the hanging protocol for importation of medical images of a patient according to the filled viewports in the workspace.

11. The computer-implemented method of claim 1, further comprising:
displaying, within a viewport filled with the first building block, a layer option for editing a stack of images associated with the first building block;
receiving a selection of the layer option;
upon receiving the selection of the layer option, displaying an layer ordering menu that includes a plurality of stacked layers corresponding to medical images;
receiving an indication to reorder the stacked layers; and
storing the reordering of stacked layers.

12. The computer-implemented method of claim 1, further comprising:
receiving a selection of a patient for which medical images are to be imported;
accessing the stored hanging protocol;
importing the medical images for the patient; and
displaying the imported medical images according to the stored hanging protocol.

13. The computer-implemented method of claim 1, wherein:
when the first building block is a single building block, one viewport is filled; and
when the first building block is a combination of building blocks, more than one viewport is filled.

14. The computer-implemented method of claim 1, wherein:
when the second building block is a single building block, one viewport is filled; and
when the second building block is a combination of building blocks, more than one viewport is filled.

* * * * *